United States Patent
Khalil et al.

(10) Patent No.: US 10,410,451 B1
(45) Date of Patent: Sep. 10, 2019

(54) SYSTEM AND METHOD FOR SECURELY CONTROLLING CONTAINER UNLOCKING BASED ON BIOMETRIC DATA

(71) Applicant: Express Scripts Strategic Development, Inc., St. Louis, MO (US)

(72) Inventors: Syed-Muasir Khalil, Austin, TX (US); Imaduldin Krad, Austin, TX (US); Ankur Kaneria, Cedar Park, TX (US); Igor Krasnykh, Round Rock, TX (US); Kerra A. Bach, Chesterfield, MO (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 0 days.

(21) Appl. No.: 15/972,452

(22) Filed: May 7, 2018

(51) Int. Cl.
G07C 9/00 (2006.01)
G16H 20/13 (2018.01)
G06F 21/32 (2013.01)

(52) U.S. Cl.
CPC ......... *G07C 9/00563* (2013.01); *G06F 21/32* (2013.01); *G16H 20/13* (2018.01); *G07C 2009/00769* (2013.01)

(58) Field of Classification Search
None
See application file for complete search history.

(56) References Cited

U.S. PATENT DOCUMENTS

| | | | |
|---|---|---|---|
| 5,616,140 A | 4/1997 | Prescott | |
| 6,138,865 A | 10/2000 | Gilmore | |
| 6,707,381 B1 * | 3/2004 | Maloney | G07C 9/00103 340/568.1 |
| 10,059,520 B2 * | 8/2018 | Joplin | G06F 19/3475 |
| 10,163,068 B2 * | 12/2018 | Hoffman | G06Q 10/083 |
| 2004/0158350 A1 | 8/2004 | Ostergaard et al. | |

(Continued)

OTHER PUBLICATIONS

SpaceSavingStorage, Secure Pharmaceutical Dispensing Cabinets & Carts for Managing Medications, Jan. 26, 2015, YouTube, (Summary attached), https://www.youtube.com/watch?v=wBO0RMpCCnc (Year: 2015).*

(Continued)

*Primary Examiner* — Carlos Garcia
(74) *Attorney, Agent, or Firm* — Harness, Dickey & Pierce, PLC

(57) ABSTRACT

A locking container access system includes (i) at least one processor and (ii) a memory storing instructions for execution on at least one processor. The instructions include establishing a connection to a locking container and obtaining an identifier from the locking container. The instructions include, in response to a user authenticating to the locking container access system, establishing a remote networking connection to an access control system, obtaining access parameters for the user from the access control system, and, in response to receiving an open instruction from the user for the locking container, performing additional operations. The additional operations include (i) requesting verification of the user based on biometric information, (ii) determining whether the identifier is included in the access parameters, and (iii) in response to the identifier being included in the access parameters and successful biometric verification of the user, transmitting an open command to the locking container.

20 Claims, 17 Drawing Sheets

(56) References Cited

U.S. PATENT DOCUMENTS

2007/0186923 A1     8/2007   Poutiatine et al.
2016/0328903 A1*   11/2016   Roberts .............. G06K 9/00087

OTHER PUBLICATIONS

SpaceSavingStorage, Secure Pharmaceutical Dispensing Cabinets & Carts for Managing Medications, Jan. 26, 2015, YouTube, (Transcript attached), https://www.youtube.com/watch?v=wBO0RMpCCnc (Year: 2015).*

* cited by examiner

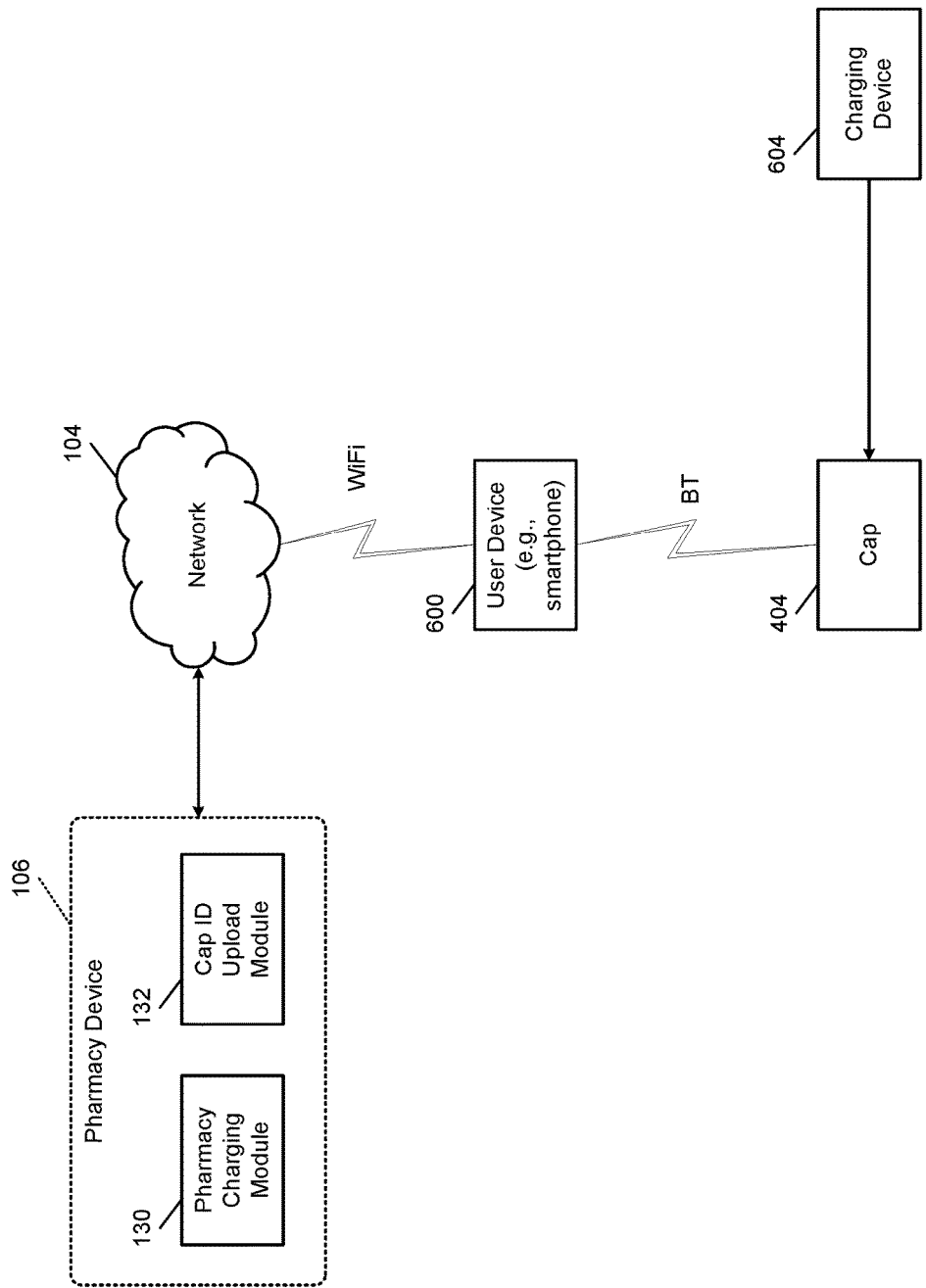

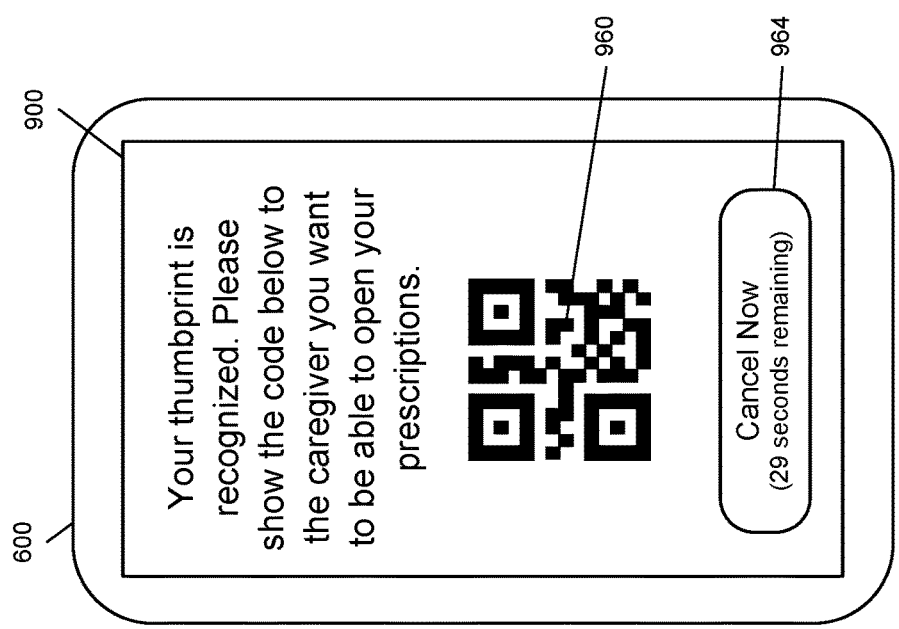

SYSTEM AND METHOD FOR SECURELY CONTROLLING CONTAINER UNLOCKING BASED ON BIOMETRIC DATA

FIELD

The present disclosure relates to drug security and, more particularly, to computerized authentication and control of access to drugs.

BACKGROUND

Misuse of prescription drugs by unauthorized users is increasingly prevalent, prompting some users with prescription drugs to hide and/or secure prescription containers within their home. Securing the prescription drugs in a locking receptacle or dispenser may be an advantageous approach to preventing unauthorized access.

While the locking receptacle can prevent easy access to the prescription drug, an unauthorized individual can procure a key through deceit or otherwise to access the locking receptacle. That is, even without permission to use a mechanical or remote control key to unlock the locking receptacle, once the unauthorized user gains access to the key, the unauthorized user also gains access to the prescription drugs.

Additionally, in general, a mechanical key is not secure enough, as an unauthorized user can easily make a copy of the mechanical key for consistent access. On the other hand, from the perspective of an authorized user, mechanical keys can be too secure since they may be lost or not returned.

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

A locking container access system includes at least one processor and a memory storing instructions for execution on at least one processor. The instructions include establishing a connection to a locking container and obtaining an identifier from the locking container. The instructions include, in response to a user authenticating to the locking container access system, establishing a remote networking connection to an access control system, obtaining access parameters for the user from the access control system, and in response to receiving an open instruction from the user for the locking container, (i) requesting verification of the user based on biometric information of the user, (ii) determining whether the identifier is included in the access parameters, and (iii) in response to determining that the identifier is included in the access parameters and successful verification of the user based on the biometric information, transmitting an open command to the locking container.

In other features, the access parameters include an expiration date and the instructions include preventing transmission of the open command subsequent to the expiration date. In other features, the access parameters include one or more times of day and the instructions include preventing transmission of the open command at a time not within the one or more times of day. In other features, the user authenticates to the locking container access system by supplying a username and password.

In other features, the instructions include, in response to a delegation instruction from the user, displaying a unique code for capture by a second device. The unique code enables access to the locking container by the second device. In other features, the instructions include establishing connections with a plurality of locking containers including the locking container; based on the access parameters, determining a set of containers associated with the user from among the plurality of locking containers; and displaying a list of the set of containers to the user for potential unlocking.

In other features, the locking container includes a bottle and a cap that attaches to the bottle. The connection is established with the cap. In other features, the open command instructs the cap to disengage from the bottle so that the cap can rotate with respect to the bottle. In other features, the locking container is a bottle including prescribed items. The access control system is maintained by a pharmacy that prescribed the bottle.

In other features, the connection is established to the locking container according to a BLUETOOTH wireless networking standard. The remote networking connection is established over the internet. In other features, the open command instructs the locking container to remain unlocked for a predetermined period of time. Transmission of the open command prevents future transmission of open commands for the predetermined period of time.

A method of accessing a locking container includes establishing a connection to the locking container and obtaining an identifier from the locking container. The method includes, in response to receiving an indication that a user has authenticated to a locking container access system, establishing a remote networking connection to an access control system and obtaining access parameters for the user from the access control system. The method includes, in response to receiving an open instruction from the user for the locking container, (i) requesting verification of the user based on biometric information of the user, (ii) determining whether the identifier is included in the access parameters, and (iii) in response to determining that the identifier is included in the access parameters and successful verification of the user based on the biometric information, transmitting an open command to the locking container.

In other features, the access parameters include an expiration date. Transmission of the open command is prevented subsequent to the expiration date. In other features, the access parameters include one or more times of day. Transmission of the open command is prevented at a time not within the one or more times of day. In other features, the user authenticates to the locking container access system by supplying a username and password.

In other features, the method includes, in response to a delegation instruction from the user, displaying a unique code for capture by a second device. The unique code enables access to the locking container by the second device. In other features, the method includes establishing connections with a plurality of locking containers including the locking container, and, based on the access parameters, determining a set of containers associated with the user from among the plurality of locking containers and displaying a list of the set of containers to the user for potential unlocking.

In other features, the locking container includes a bottle and a cap that attaches to the bottle. The connection is established with the cap. In other features, the open command instructs the cap to disengage from the bottle so that the cap can rotate with respect to the bottle. In other features, the locking container is a bottle including prescribed items. The access control system is maintained by a pharmacy that prescribed the bottle. In other features, the connection to the locking container is established according to a BLUETOOTH wireless networking standard. The remote networking connection is established over the internet. In other features, the open command instructs the locking container to remain unlocked for a predetermined period of time. Transmission of the open command prevents future transmission of open commands for the predetermined period of time.

A non-transitory computer-readable medium stores processor-executable instructions. The instructions include establishing a connection to a locking container and obtaining an identifier from the locking container. The instructions include, in response to receiving an indication that a user has authenticated to a locking container access system, establishing a remote networking connection to an access control system and obtaining access parameters for the user from the access control system. The instructions include, in response to receiving an open instruction from the user for the locking container, (i) requesting verification of the user based on biometric information of the user, (ii) determining whether the identifier is included in the access parameters, and (iii) in response to determining that the identifier is included in the access parameters and successful verification of the user based on the biometric information, transmitting an open command to the locking container.

Further areas of applicability of the present disclosure will become apparent from the detailed description, the claims, and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings.

FIG. 6B is a functional block diagram of an example implementation of a wireless cap charging system located at a user's residence.

FIG. 9G is an example prescription application user delegation screen of the prescription application.

In the drawings, reference numbers may be reused to identify similar and/or identical elements.

DETAILED DESCRIPTION

Introduction

Figure 1:
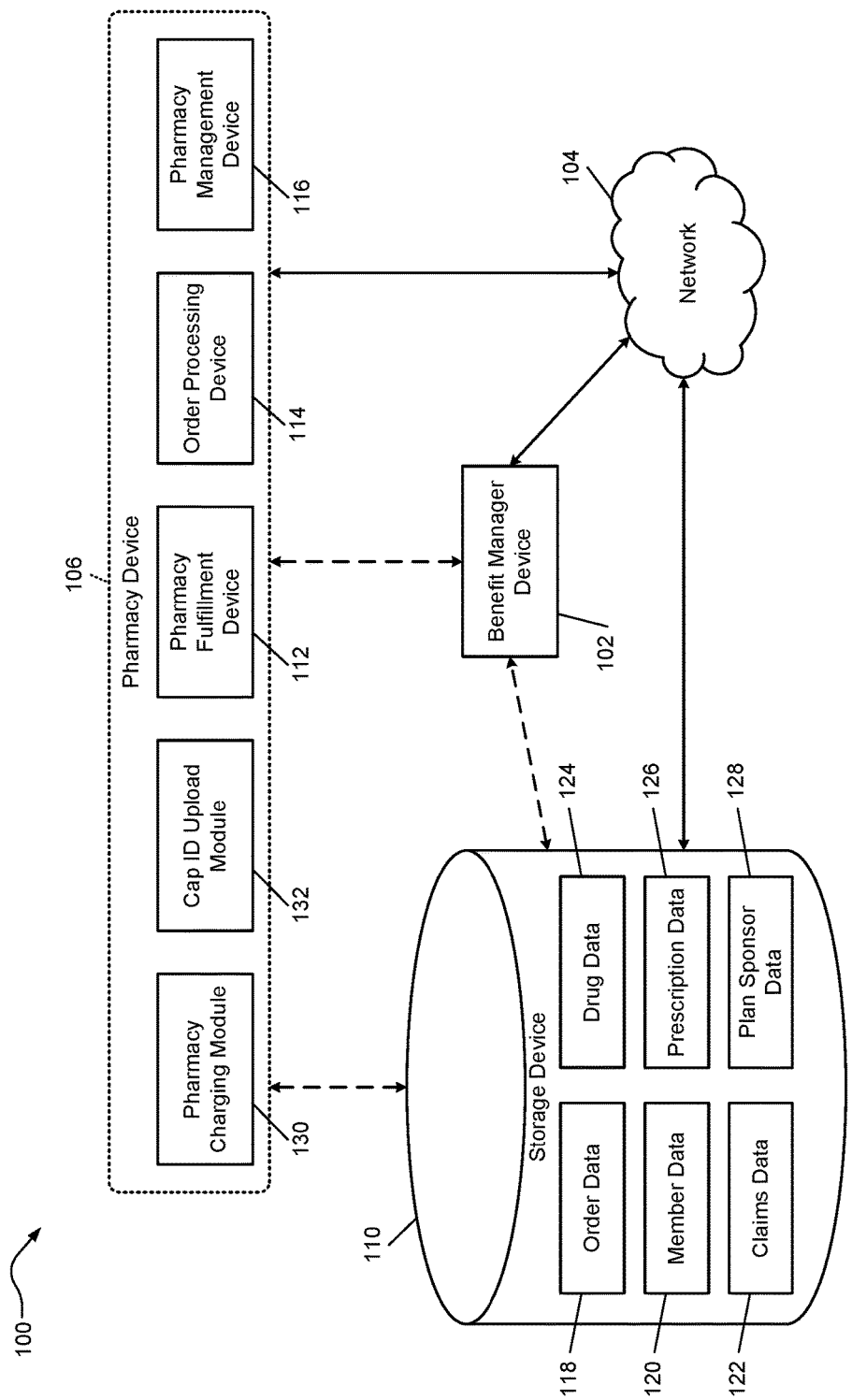
FIG. 1 is a functional block diagram of an example system including a high-volume pharmacy.

To restrict access to a prescription container, a user device requests biometric input from a user to verify the user's identity before unlocking the prescription container. In various implementations, the user can unlock the prescription container by selecting a corresponding option displayed on a user interface of a prescription application downloaded on the user device.

The user creates or logs into an account on the prescription application, allowing the prescription application to retrieve the user's prescription information from a pharmacy. When the user selects an OPEN option for the prescription container, the prescription application requests biometric input from the user before sending an open prescription control signal to the corresponding prescription container. The prescription application leverages an existing biometric input device of the user device. For example, the user device may include a fingerprint scanner, a front-facing camera for facial recognition, a heart rate monitor, etc.

In various implementations, a smart cap (or, in other implementations, a smart bottle or smart medication dispensing device) may be programmed with a pharmacy public key of a pharmacy public-private key pair, which the smart cap will then trust. The smart cap can use the pharmacy public key to verify that the pharmacy private key was used to sign an instruction and then act upon that verified instruction. The pharmacy private key may be maintained in secured storage, such as a hardware security module (HSM).

When a user authenticates to the pharmacy from a first device (such as a smartphone), the pharmacy may sign an instruction indicating that smart caps corresponding to prescriptions for that user should trust the first device. The first device may then require biometric verification of the user each time the first device transmits an open instruction to the smart cap.

A user may be able to delegate prescription opening authority to a caregiver. When the caregiver authenticates to the pharmacy from a second device on behalf of the user, the pharmacy may sign a delegation instruction for distribution to smart caps corresponding to prescriptions for that user. The delegation instruction indicates that the smart caps should trust the second device.

The caregiver may authenticate to the pharmacy by presenting a token received from the user. For example, the user may cause the prescription application to display a unique code (for example, a QR code) on the first device. The second device can capture the QR code via a camera and present the code back to the first device or to the pharmacy. The code may be generated and verified by the pharmacy, or verified by the first device. Either the pharmacy or the first device may then send the delegation instruction to the smart cap to trust the second device. Once the smart cap trusts the second device, the caregiver can access a prescription by authenticating to the second device (such as with one or more biometrics).

The delegation instruction may restrict the number of times the caregiver can access the prescription. For example, a cumulative total limit may be set. In other implementations, the limit may be per day, and may be based on an expected number of dispensations to be performed by the caregiver. For a prescription that will be dispensed 4 times per day, but only once in the evening, an evening caregiver may only be permitted to access the prescription once per day.

To remove the caregiver's access (such as when the caregiver moves to a new job), the first device or the pharmacy can instruct the smart cap to no longer trust the second device. In various implementations, the user may specify a fixed expiration date or time period for delegation. The smart cap will then automatically revoke the caregiver's access even in the absence of a manual revocation instruction. For example, the user may specify when the caregiver will be replaced by a new caregiver, revoking access on the day of transition or the day after. In other implementations, the time period for delegation may be limited to a certain time period, such as 4 weeks. In this way, the caregiver's access is time-limited even if the user forgets to manually revoke access. The time period may be set by the user, and a maximum time period may be imposed by the pharmacy.

High-Volume Pharmacy

FIG. 1 is a block diagram of an example implementation of a system 100 for a high-volume pharmacy. While the system 100 is generally described as being deployed in a high-volume pharmacy or a fulfillment center (for example, a mail order pharmacy, a direct delivery pharmacy, etc.), the system 100 and/or components of the system 100 may otherwise be deployed (for example, in a lower-volume pharmacy, etc.). A high-volume pharmacy may be a pharmacy that is capable of filling at least some prescriptions mechanically. The system 100 may include a benefit manager device 102 and a pharmacy device 106 in communication with each other directly and/or over a network 104. The system 100 may also include a storage device 110.

The benefit manager device 102 is a device operated by an entity that is at least partially responsible for creation and/or management of the pharmacy or drug benefit. While the entity operating the benefit manager device 102 is typically a pharmacy benefit manager (PBM), other entities may operate the benefit manager device 102 on behalf of themselves or other entities (such as PBMs). For example, the benefit manager device 102 may be operated by a health plan, a retail pharmacy chain, a drug wholesaler, a data analytics or other type of software-related company, etc. In some implementations, a PBM that provides the pharmacy benefit may provide one or more additional benefits including a medical or health benefit, a dental benefit, a vision benefit, a wellness benefit, a radiology benefit, a pet care benefit, an insurance benefit, a long term care benefit, a nursing home benefit, etc. The PBM may, in addition to its PBM operations, operate one or more pharmacies. The pharmacies may be retail pharmacies, mail order pharmacies, etc.

Some of the operations of the PBM that operates the benefit manager device 102 may include the following activities and processes. A member (or a person on behalf of the member) of a pharmacy benefit plan may obtain a prescription drug at a retail pharmacy location (e.g., a location of a physical store) from a pharmacist or a pharmacist technician. The member may also obtain the prescription drug through mail order drug delivery from a mail order pharmacy location, such as the system 100. In some implementations, the member may obtain the prescription drug directly or indirectly through the use of a machine, such as a kiosk, a vending unit, a mobile electronic device, or a different type of mechanical device, electrical device, electronic communication device, and/or computing device. Such a machine may be filled with the prescription drug in prescription packaging, which may include multiple prescription components, by the system 100. The pharmacy benefit plan is administered by or through the benefit manager device 102.

The member may have a copayment for the prescription drug that reflects an amount of money that the member is responsible to pay the pharmacy for the prescription drug. The money paid by the member to the pharmacy may come from, as examples, personal funds of the member, a health savings account (HSA) of the member or the member's family, a health reimbursement arrangement (HRA) of the member or the member's family, or a flexible spending account (FSA) of the member or the member's family. In some instances, an employer of the member may directly or indirectly fund or reimburse the member for the copayments.

The amount of the copayment required by the member may vary across different pharmacy benefit plans having different plan sponsors or clients and/or for different prescription drugs. The member's copayment may be a flat copayment (in one example, $10), coinsurance (in one example, 10%), and/or a deductible (for example, responsibility for the first $500 of annual prescription drug expense, etc.) for certain prescription drugs, certain types and/or classes of prescription drugs, and/or all prescription drugs. The copayment may be stored in the storage device 110 or determined by the benefit manager device 102.

In some instances, the member may not pay the copayment or may only pay a portion of the copayment for the prescription drug. For example, if a usual and customary cost for a generic version of a prescription drug is $4, and the member's flat copayment is $20 for the prescription drug, the member may only need to pay $4 to receive the prescription drug. In another example involving a worker's compensation claim, no copayment may be due by the member for the prescription drug.

In addition, copayments may also vary based on different delivery channels for the prescription drug. For example, the copayment for receiving the prescription drug from a mail order pharmacy location may be less than the copayment for receiving the prescription drug from a retail pharmacy location.

In conjunction with receiving a copayment (if any) from the member and dispensing the prescription drug to the member, the pharmacy submits a claim to the PBM for the prescription drug. After receiving the claim, the PBM (such as by using the benefit manager device 102) may perform certain adjudication operations including verifying eligibility for the member, identifying/reviewing an applicable formulary for the member to determine any appropriate copayment, coinsurance, and deductible for the prescription drug, and performing a drug utilization review (DUR) for the member. Further, the PBM may provide a response to the pharmacy (for example, the pharmacy system 100) following performance of at least some of the aforementioned operations.

As part of the adjudication, a plan sponsor (or the PBM on behalf of the plan sponsor) ultimately reimburses the pharmacy for filling the prescription drug when the prescription drug was successfully adjudicated. The aforementioned adjudication operations generally occur before the copayment is received and the prescription drug is dispensed. However in some instances, these operations may occur simultaneously, substantially simultaneously, or in a different order. In addition, more or fewer adjudication operations may be performed as at least part of the adjudication process.

The amount of reimbursement paid to the pharmacy by a plan sponsor and/or money paid by the member may be determined at least partially based on types of pharmacy networks in which the pharmacy is included. In some implementations, the amount may also be determined based on other factors. For example, if the member pays the pharmacy for the prescription drug without using the prescription or drug benefit provided by the PBM, the amount of money paid by the member may be higher than when the member uses the prescription or drug benefit. In some implementations, the amount of money received by the pharmacy for dispensing the prescription drug and for the prescription drug itself may be higher than when the member uses the prescription or drug benefit. Some or all of the foregoing operations may be performed by executing instructions stored in the benefit manager device 102 and/or an additional device.

Examples of the network 104 include a Global System for Mobile Communications (GSM) network, a code division multiple access (CDMA) network, 3rd Generation Partnership Project (3GPP), an Internet Protocol (IP) network, a Wireless Application Protocol (WAP) network, or an IEEE 802.11 standards network, as well as various combinations of the above networks. The network 104 may include an optical network. The network 104 may be a local area network or a global communication network, such as the Internet. In some implementations, the network 104 may include a network dedicated to prescription orders: a prescribing network such as the electronic prescribing network operated by Surescripts of Arlington, Va.

Moreover, although the system shows a single network 104, multiple networks can be used. The multiple networks may communicate in series and/or parallel with each other to link the devices 102-110.

The pharmacy device 106 may be a device associated with a retail pharmacy location (e.g., an exclusive pharmacy location, a grocery store with a retail pharmacy, or a general sales store with a retail pharmacy) or other type of pharmacy location at which a member attempts to obtain a prescription. The pharmacy may use the pharmacy device 106 to submit the claim to the PBM for adjudication.

Additionally, in some implementations, the pharmacy device 106 may enable information exchange between the pharmacy and the PBM. For example, this may allow the sharing of member information such as drug history that may allow the pharmacy to better service a member (for example, by providing more informed therapy consultation and drug interaction information). In some implementations, the benefit manager device 102 may track prescription drug fulfillment and/or other information for users that are not members, or have not identified themselves as members, at the time (or in conjunction with the time) in which they seek to have a prescription filled at a pharmacy.

The pharmacy device 106 may include a pharmacy fulfillment device 112, an order processing device 114, a pharmacy management device 116, and a pharmacy charging module 130 in communication with each other directly and/or over the network 104.

The order processing device 114 may receive information regarding filling prescriptions and may direct an order component to one or more devices of the pharmacy fulfillment device 112 at a pharmacy. The pharmacy fulfillment device 112 may fulfill, dispense, aggregate, and/or pack the order components of the prescription drugs in accordance with one or more prescription orders directed by the order processing device 114.

In general, the order processing device 114 is a device located within or otherwise associated with the pharmacy to enable the pharmacy fulfilment device 112 to fulfill a prescription and dispense prescription drugs. In some implementations, the order processing device 114 may be an external order processing device separate from the pharmacy and in communication with other devices located within the pharmacy.

For example, the external order processing device may communicate with an internal pharmacy order processing device and/or other devices located within the system 100. In some implementations, the external order processing device may have limited functionality (e.g., as operated by a user requesting fulfillment of a prescription drug), while the internal pharmacy order processing device may have greater functionality (e.g., as operated by a pharmacist).

The order processing device 114 may track the prescription order as it is fulfilled by the pharmacy fulfillment device 112. The prescription order may include one or more prescription drugs to be filled by the pharmacy. The order processing device 114 may make pharmacy routing decisions and/or order consolidation decisions for the particular prescription order. The pharmacy routing decisions include what device(s) in the pharmacy are responsible for filling or otherwise handling certain portions of the prescription order. The order consolidation decisions include whether portions of one prescription order or multiple prescription orders should be shipped together for a user or a user family. The order processing device 114 may also track and/or schedule literature or paperwork associated with each prescription order or multiple prescription orders that are being shipped together. In some implementations, the order processing device 114 may operate in combination with the pharmacy management device 116.

The order processing device 114 may include circuitry, a processor, a memory to store data and instructions, and communication functionality. The order processing device 114 is dedicated to performing processes, methods, and/or instructions described in this application. Other types of electronic devices may also be used that are specifically configured to implement the processes, methods, and/or instructions described in further detail below.

In some implementations, at least some functionality of the order processing device 114 may be included in the pharmacy management device 116. The order processing device 114 may be in a client-server relationship with the pharmacy management device 116, in a peer-to-peer relationship with the pharmacy management device 116, or in a different type of relationship with the pharmacy management device 116. The order processing device 114 and/or the pharmacy management device 116 may communicate directly (for example, such as by using a local storage) and/or through the network 104 (such as by using a cloud storage configuration, software as a service, etc.) with the storage device 110.

The storage device 110 may include: non-transitory storage (for example, memory, hard disk, CD-ROM, etc.) in communication with the benefit manager device 102 and/or the pharmacy device 106 directly and/or over the network 104. The non-transitory storage may store order data 118, member data 120, claims data 122, drug data 124, prescription data 126, and/or plan sponsor data 128. Further, the system 100 may include additional devices, which may communicate with each other directly or over the network 104.

The order data 118 may be related to a prescription order. The order data may include type of the prescription drug (for example, drug name and strength) and quantity of the prescription drug. The order data 118 may also include data used for completion of the prescription, such as prescription materials. In general, prescription materials include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, etc. The order data 118 may be used by a high-volume fulfillment center to fulfill a pharmacy order.

In some implementations, the order data 118 includes verification information associated with fulfillment of the prescription in the pharmacy. For example, the order data 118 may include videos and/or images taken of (i) the prescription drug prior to dispensing, during dispensing, and/or after dispensing, (ii) the prescription container (for example, a prescription container and sealing lid, prescription packaging, etc.) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/or (iv) the fulfillment process within the pharmacy. Other types of verification information such as barcode data read from pallets, bins, trays, or carts used to transport prescriptions within the pharmacy may also be stored as order data 118.

The member data 120 includes information regarding the members associated with the PBM. The information stored as member data 120 may include personal information, personal health information, protected health information, etc. Examples of the member data 120 include name, address, telephone number, e-mail address, prescription drug history, etc. The member data 120 may include a plan sponsor identifier that identifies the plan sponsor associated with the member and/or a member identifier that identifies the member to the plan sponsor. The member data 120 may include a member identifier that identifies the plan sponsor associated with the user and/or a user identifier that identifies the user to the plan sponsor. The member data 120 may also include dispensation preferences such as type of label, type of cap, message preferences, language preferences, etc.

The member data 120 may be accessed by various devices in the pharmacy (for example, the high-volume fulfillment center, etc.) to obtain information used for fulfillment and shipping of prescription orders. In some implementations, an external order processing device operated by or on behalf of a member may have access to at least a portion of the member data 120 for review, verification, or other purposes.

In some implementations, the member data 120 may include information for persons who are users of the pharmacy but are not members in the pharmacy benefit plan being provided by the PBM. For example, these users may obtain drugs directly from the pharmacy, through a private label service offered by the pharmacy, the high-volume fulfillment center, or otherwise. In general, the use of the terms "member" and "user" may be used interchangeably.

The claims data 122 includes information regarding pharmacy claims adjudicated by the PBM under a drug benefit program provided by the PBM for one or more plan sponsors. In general, the claims data 122 includes an identification of the client that sponsors the drug benefit program under which the claim is made, and/or the member that purchased the prescription drug giving rise to the claim, the prescription drug that was filled by the pharmacy (e.g., the national drug code number, etc.), the dispensing date, generic indicator, generic product identifier (GPI) number, medication class, the cost of the prescription drug provided under the drug benefit program, the copayment/coinsurance amount, rebate information, and/or member eligibility, etc. Additional information may be included.

In some implementations, other types of claims beyond prescription drug claims may be stored in the claims data 122. For example, medical claims, dental claims, wellness claims, or other types of health-care-related claims for members may be stored as a portion of the claims data 122.

In some implementations, the claims data 122 includes claims that identify the members with whom the claims are associated. Additionally or alternatively, the claims data 122 may include claims that have been de-identified (that is, associated with a unique identifier but not with a particular, identifiable member).

The drug data 124 may include drug name (e.g., technical name and/or common name), other names by which the drug is known, active ingredients, an image of the drug (such as in pill form), etc. The drug data 124 may include information associated with a single medication or multiple medications.

The prescription data 126 may include information regarding prescriptions that may be issued by prescribers on behalf of users, who may be members of the pharmacy benefit plan—for example, to be filled by a pharmacy. Examples of the prescription data 126 include user names, medication or treatment (such as lab tests), dosing information, etc. The prescriptions may include electronic prescriptions or paper prescriptions that have been scanned. In some implementations, the dosing information reflects a frequency of use (e.g., once a day, twice a day, before each meal, etc.) and a duration of use (e.g., a few days, a week, a few weeks, a month, etc.).

In some implementations, the order data 118 may be linked to associated member data 120, claims data 122, drug data 124, and/or prescription data 126.

The plan sponsor data 128 includes information regarding the plan sponsors of the PBM. Examples of the plan sponsor data 128 include company name, company address, contact name, contact telephone number, contact e-mail address, etc.

Figure 2:
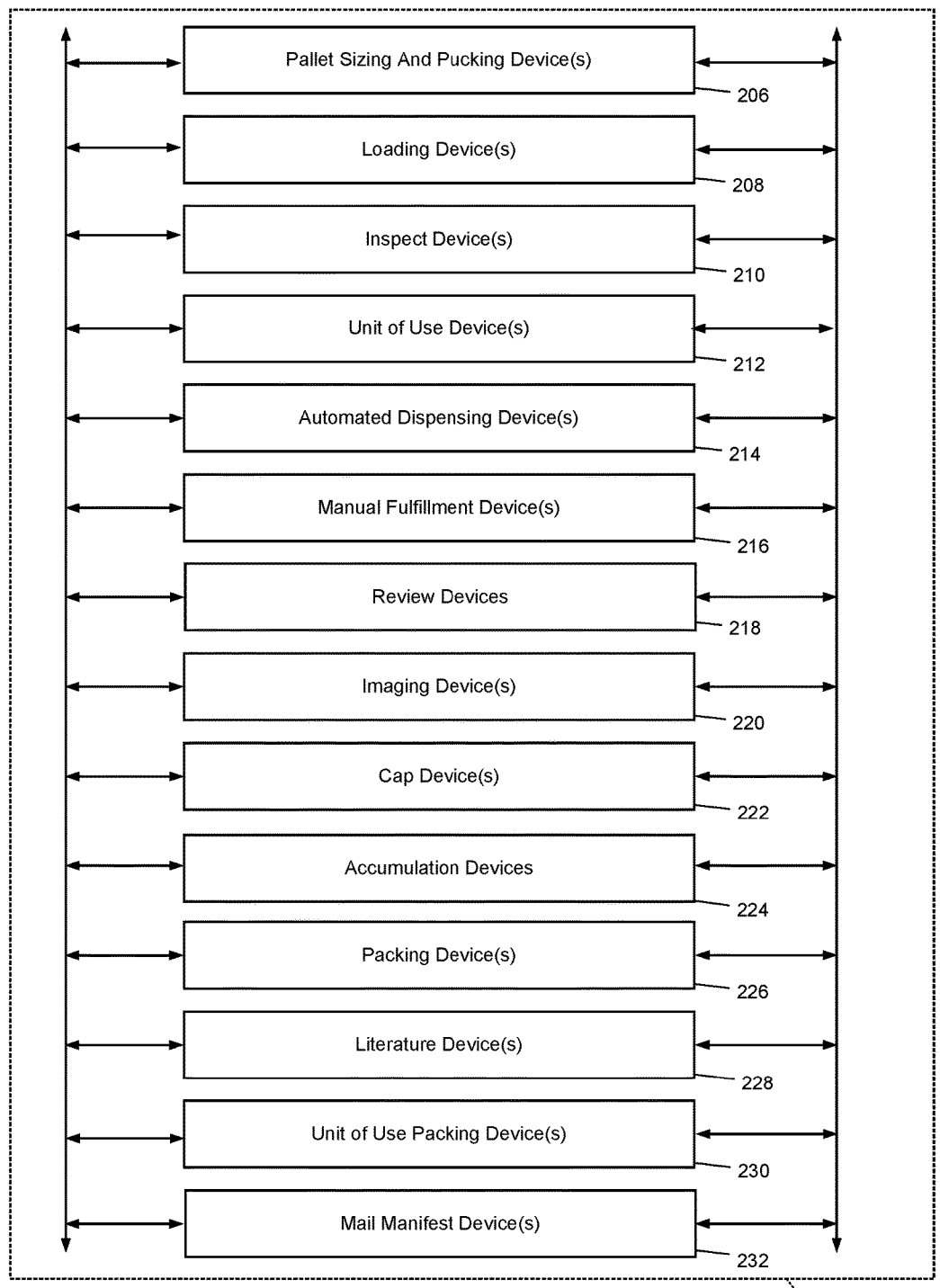
FIG. 2 is a functional block diagram of an example pharmacy fulfillment device, which may be deployed within the system of FIG. 1.

FIG. 2 illustrates the pharmacy fulfillment device 112 according to an example implementation. The pharmacy fulfillment device 112 may be used to process and fulfill prescriptions and prescription orders. After fulfillment, the fulfilled prescriptions are packed for shipping.

The pharmacy fulfillment device 112 may include devices in communication with the benefit manager device 102, the order processing device 114, and/or the storage device 110, directly or over the network 104. Specifically, the pharmacy fulfillment device 112 may include pallet sizing and pucking device(s) 206, loading device(s) 208, inspect device(s) 210, unit of use device(s) 212, automated dispensing device(s) 214, manual fulfillment device(s) 216, review devices 218, imaging device(s) 220, cap device(s) 222, accumulation devices 224, packing device(s) 226, literature device(s) 228, unit of use packing device(s) 230, and mail manifest device(s) 232. Further, the pharmacy fulfillment device 112 may include additional devices, which may communicate with each other directly or over the network 104.

In some implementations, operations performed by one of these devices 206-232 may be performed sequentially, or in parallel with the operations of another device as may be coordinated by the order processing device 114. In some implementations, the order processing device 114 tracks a prescription with the pharmacy based on operations performed by one or more of the devices 206-232.

In some implementations, the pharmacy fulfillment device 112 may transport prescription drug containers, for example, among the devices 206-232 in the high-volume fulfillment center, by use of pallets. The pallet sizing and pucking device 206 may configure pucks in a pallet. A pallet may be a transport structure for a number of prescription containers, and may include a number of cavities. A puck may be placed in one or more than one of the cavities in a pallet by the pallet sizing and pucking device 206. The puck may include a receptacle sized and shaped to receive a prescription container. Such containers may be supported by the pucks during carriage in the pallet. Different pucks may have differently sized and shaped receptacles to accommodate containers of differing sizes, as may be appropriate for different prescriptions.

The arrangement of pucks in a pallet may be determined by the order processing device 114 based on prescriptions that the order processing device 114 decides to launch. The arrangement logic may be implemented directly in the pallet sizing and pucking device 206. Once a prescription is set to be launched, a puck suitable for the appropriate size of container for that prescription may be positioned in a pallet by a robotic arm or pickers. The pallet sizing and pucking device 206 may launch a pallet once pucks have been configured in the pallet.

The loading device 208 may load prescription containers into the pucks on a pallet by a robotic arm, a pick and place mechanism (also referred to as pickers), etc. In various implementations, the loading device 208 has robotic arms or pickers to grasp a prescription container and move it to and from a pallet or a puck. The loading device 208 may also print a label that is appropriate for a container that is to be loaded onto the pallet, and apply the label to the container. The pallet may be located on a conveyor assembly during these operations (e.g., at the high-volume fulfillment center, etc.).

The inspect device 210 may verify that containers in a pallet are correctly labeled and in the correct spot on the pallet. The inspect device 210 may scan the label on one or more containers on the pallet. Labels of containers may be scanned or imaged in full or in part by the inspect device 210. Such imaging may occur after the container has been lifted out of its puck by a robotic arm, picker, etc., or may be otherwise scanned or imaged while retained in the puck.

In some implementations, images and/or video captured by the inspect device 210 may be stored in the storage device 110 as order data 118.

The unit of use device 212 may temporarily store, monitor, label, and/or dispense unit of use products. In general, unit of use products are prescription drug products that may be delivered to a user or member without being repackaged at the pharmacy. These products may include pills in a container, pills in a blister pack, inhalers, etc. Prescription drug products dispensed by the unit of use device 212 may be packaged individually or collectively for shipping, or may be shipped in combination with other prescription drugs dispensed by other devices in the high-volume fulfillment center.

At least some of the operations of the devices 206-232 may be directed by the order processing device 114. For example, the manual fulfillment device 216, the review device 218, the automated dispensing device 214, and/or the packing device 226, etc. may receive instructions provided by the order processing device 114.

The automated dispensing device 214 may include one or more devices that dispense prescription drugs or pharmaceuticals into prescription containers in accordance with one or multiple prescription orders. In general, the automated dispensing device 214 may include mechanical and electronic components with, in some implementations, software and/or logic to facilitate pharmaceutical dispensing that would otherwise be performed in a manual fashion by a pharmacist and/or pharmacist technician. For example, the automated dispensing device 214 may include high-volume fillers that fill a number of prescription drug types at a rapid rate and blister pack machines that dispense and pack drugs into a blister pack. Prescription drugs dispensed by the automated dispensing devices 214 may be packaged individually or collectively for shipping, or may be shipped in combination with other prescription drugs dispensed by other devices in the high-volume fulfillment center.

The manual fulfillment device 216 controls how prescriptions are manually fulfilled. For example, the manual fulfillment device 216 may receive or obtain a container and enable fulfillment of the container by a pharmacist or pharmacy technician. In some implementations, the manual fulfillment device 216 provides the filled container to another device in the pharmacy fulfillment devices 112 to be joined with other containers in a prescription order for a user or member.

In general, manual fulfillment may include operations at least partially performed by a pharmacist or a pharmacy technician. For example, a person may retrieve a supply of the prescribed drug, may make an observation, may count out a prescribed quantity of drugs and place them into a prescription container, etc. Some portions of the manual fulfillment process may be automated by use of a machine. For example, counting of capsules, tablets, or pills may be at least partially automated (such as through use of a pill counter). Prescription drugs dispensed by the manual fulfillment device 216 may be packaged individually or collectively for shipping, or may be shipped in combination with other prescription drugs dispensed by other devices in the high-volume fulfillment center.

The review device 218 may process prescription containers to be reviewed by a pharmacist for proper pill count, exception handling, prescription verification, etc. Fulfilled prescriptions may be manually reviewed and/or verified by a pharmacist, as may be required by state or local law. A pharmacist or other licensed pharmacy person who may dispense certain drugs in compliance with local and/or other laws may operate the review device 218 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been canceled, containers with defects, etc. In an example, the manual review can be performed at a manual review station.

The imaging device 220 may image containers once they have been filled with pharmaceuticals. The imaging device 220 may measure a fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon. The images may be transmitted to the order processing device 114 and/or stored in the storage device 110 as part of the order data 118.

The cap device 222 may be used to cap or otherwise seal a prescription container. In some implementations, the cap device 222 may secure a prescription container with a type of cap in accordance with a user preference (e.g., a preference regarding child resistance, etc.), a plan sponsor preference, a prescriber preference, etc. The cap device 222 may also etch a message into the cap, although this process may be performed by a subsequent device in the high-volume fulfillment center.

The accumulation device 224 accumulates various containers of prescription drugs in a prescription order. The accumulation device 224 may accumulate prescription containers from various devices or areas of the pharmacy. For example, the accumulation device 224 may accumulate prescription containers from the unit of use device 212, the automated dispensing device 214, the manual fulfillment device 216, and the review device 218. The accumulation device 224 may be used to group the prescription containers prior to shipment to the member.

The literature device 228 prints, or otherwise generates, literature to include with each prescription drug order. The literature may be printed on multiple sheets of substrates, such as paper, coated paper, printable polymers, or combinations of the above substrates. The literature printed by the literature device 228 may include information required to accompany the prescription drugs included in a prescription order, other information related to prescription drugs in the order, financial information associated with the order (for example, an invoice or an account statement), etc.

In some implementations, the literature device 228 folds or otherwise prepares the literature for inclusion with a prescription drug order (e.g., in a shipping container). In other implementations, the literature device 228 prints the literature and is separate from another device that prepares the printed literature for inclusion with a prescription order.

The packing device 226 packages the prescription order in preparation for shipping the order. The packing device 226 may box, bag, or otherwise package the fulfilled prescription order for delivery. The packing device 226 may further place inserts (e.g., literature or other papers, etc.) into the packaging received from the literature device 228. For example, bulk prescription orders may be shipped in a box, while other prescription orders may be shipped in a bag, which may be a wrap seal bag.

The packing device 226 may label the box or bag with an address and a recipient's name. The label may be printed and affixed to the bag or box, be printed directly onto the bag or box, or otherwise associated with the bag or box. The packing device 226 may sort the box or bag for mailing in an efficient manner (e.g., sort by delivery address, etc.). The packing device 226 may include ice or temperature sensitive elements for prescriptions that are to be kept within a temperature range during shipping (for example, this may be necessary in order to retain efficacy). The ultimate package may then be shipped through postal mail, through a mail order delivery service that ships via ground and/or air (e.g., UPS, FEDEX, or DHL, etc.), through a delivery service, through a locker box at a shipping site (e.g., AMAZON locker or a PO Box, etc.), or otherwise.

The unit of use packing device 230 packages a unit of use prescription order in preparation for shipping the order. The unit of use packing device 230 may include manual scanning of containers to be bagged for shipping to verify each container in the order. In an example implementation, the manual scanning may be performed at a manual scanning station. The pharmacy fulfillment device 112 may also include a mail manifest device 232 to print mailing labels used by the packing device 226 and may print shipping manifests and packing lists.

While the pharmacy fulfillment device 112 in FIG. 2 is shown to include single devices 206-232, multiple devices may be used. When multiple devices are present, the multiple devices may be of the same device type or models, or may be a different device type or model. The types of devices 206-232 shown in FIG. 2 are example devices. In other configurations of the system 100, lesser, additional, or different types of devices may be included.

Moreover, multiple devices may share processing and/or memory resources. The devices 206-232 may be located in the same area or in different locations. For example, the devices 206-232 may be located in a building or set of adjoining buildings. The devices 206-232 may be interconnected (such as by conveyors), networked, and/or otherwise in contact with one another or integrated with one another (e.g., at the high-volume fulfillment center, etc.). In addition, the functionality of a device may be split among a number of discrete devices and/or combined with other devices.

Figure 3:
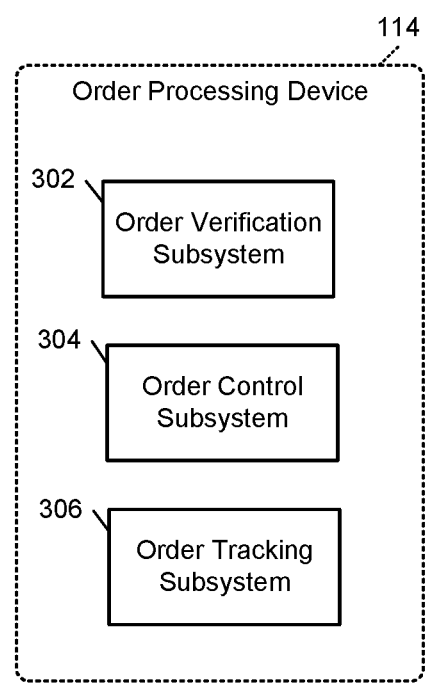
FIG. 3 is a functional block diagram of an example order processing device, which may be deployed within the system of FIG. 1.

FIG. 3 illustrates the order processing device 114 according to an example implementation. The order processing device 114 may be used by one or more operators to generate prescription orders, make routing decisions, make prescription order consolidation decisions, track literature with the system 100, and/or view order status and other order related information. For example, the prescription order may be comprised of order components.

The order processing device 114 may receive instructions to fulfill an order without operator intervention. An order component may include a prescription drug fulfilled by use of a container through the system 100. The order processing device 114 may include an order verification subsystem 302, an order control subsystem 304, and/or an order tracking subsystem 306. Other subsystems may also be included in the order processing device 114.

The order verification subsystem 302 may communicate with the benefit manager device 102 to verify the eligibility of the member and review the formulary to determine appropriate copayment, coinsurance, and deductible for the prescription drug and/or perform a DUR (drug utilization review). Other communications between the order verification subsystem 302 and the benefit manager device 102 may be performed for a variety of purposes.

The order control subsystem 304 controls various movements of the containers and/or pallets along with various filling functions during their progression through the system 100. In some implementations, the order control subsystem 304 may identify the prescribed drug in one or more than one prescription orders as capable of being fulfilled by the automated dispensing device 214. The order control subsystem 304 may determine which prescriptions are to be launched and may determine that a pallet of automated-fill containers is to be launched.

The order control subsystem 304 may determine that an automated-fill prescription of a specific pharmaceutical is to be launched and may examine a queue of orders awaiting fulfillment for other prescription orders, which will be filled with the same pharmaceutical. The order control subsystem 304 may then launch orders with similar automated-fill pharmaceutical needs together in a pallet to the automated dispensing device 214. As the devices 206-232 may be interconnected by a system of conveyors or other container movement systems, the order control subsystem 304 may control various conveyors: for example, to deliver the pallet from the loading device 208 to the manual fulfillment device 216 from the literature device 228, paperwork as needed to fill the prescription.

The order tracking subsystem 306 may track a prescription order during its progress toward fulfillment. The order tracking subsystem 306 may track, record, and/or update order history, order status, etc. The order tracking subsystem 306 may store data locally (for example, in a memory) or as a portion of the order data 118 stored in the storage device 110.

Locking Cap

Figure 4:
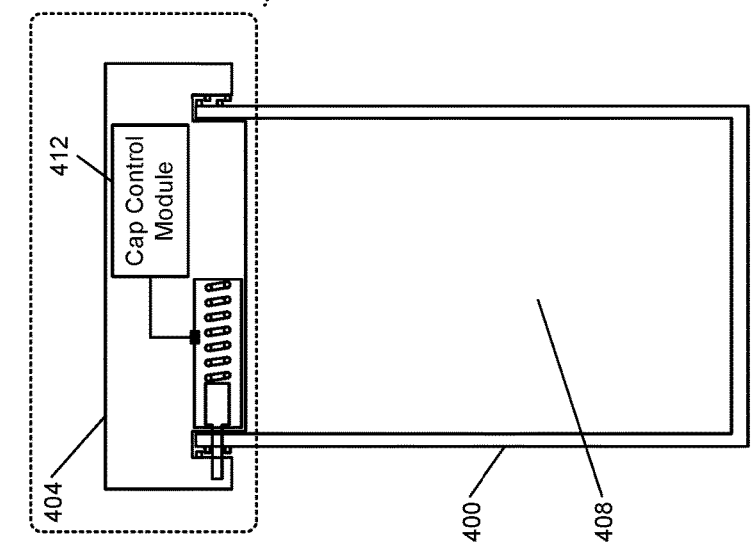
FIG. 4 is a graphical representation of a side view of an example container including an example locking cap.

FIG. 4 is a graphical representation of a side view of a container 400 including a cap 404 capable of being locked and unlocked. The container 400 defines a cavity 408 capable of storing a prescription, such as pills or another form of prescribed medical equipment (for example, patches, syringes, etc.). The cap 404 includes a cap control module 412 configured to control access to the contents of the container 400.

Figure 5A:
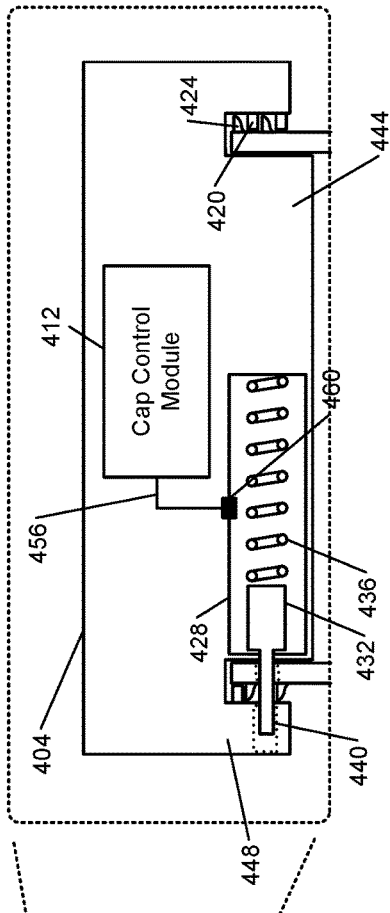
FIG. 5A is a graphical representation of an expanded side view of the cap of FIG. 4 in a locked position.

FIG. 5A is an expanded side view of the cap 404 of FIG. 4 in a locked state. As an example only, FIG. 5A depicts the cap 404 having square threads 420 and the container 400 having tapered threads 424. The threads 420 and 424 engage as the cap 404 is screwed onto the container 400.

The cap 404 includes two portions: an inside portion 444 positioned inside the cavity 408 of the container 400 when the cap 404 is secured on the container 400 and an outside portion 448 remaining outside the container 400. The outside portion 448 surrounds a circumference of the container 400. The cap 404 includes a solenoid 428 as a locking mechanism. The solenoid 428 includes a plunger 432 and a spring 436. The spring 436 presses the plunger 432 outward from the solenoid 428. In the locked position, the spring 436 is extended and an end 440 of the plunger 432 rests in a pocket 452 (shown in FIG. 5B) defined by the outside portion 448 of the cap 404; the plunger 432 extends through aperture 454 (shown in FIG. 5B) of the container 400, preventing rotation of the cap 404 with respect to the container 400.

The cap control module 412 is connected to the solenoid 428 via a cable 456 through a port 460, which may be a hermetic seal including a terminal for the cable 456 to connect to a winding (not shown) of the solenoid 428. The cap control module 412 includes a battery that is selectively connected to the cable 456. When current is not passing through the cable 456, the spring 436 remains extended and the plunger 432 rests in the pocket 452, locking the cap 404 on the container 400.

Figure 5B:
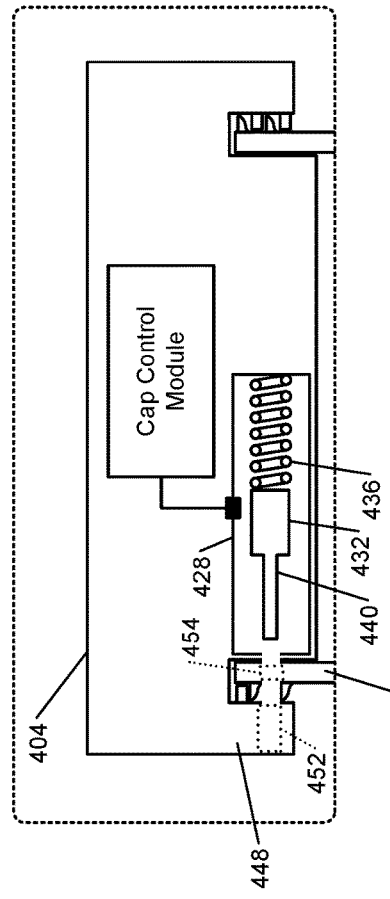
FIG. 5B is a graphical representation of an expanded side view of the cap of FIG. 4 in an unlocked position.

FIG. 5B is an expanded side view of the cap of FIG. 4 in an unlocked state. When the cap control module 412 applies a current to the solenoid 428, an electromagnetic field is created and the plunger 432 is pulled into the solenoid 428, compressing the spring 436. The plunger 432 slides out of the pocket 452.

In various implementations, the solenoid 428 may be configured so that the plunger 432 will not extend until the cap 404 is secured on the container 400—otherwise, the plunger 432 may prevent the cap 404 from being secured back on the container 400. In various implementations, the cap 404 may include a sensor that detects fastening of the cap 404 to the container 400 and maintains power to the solenoid 428 until fastening is detected.

Control

Figure 6A:
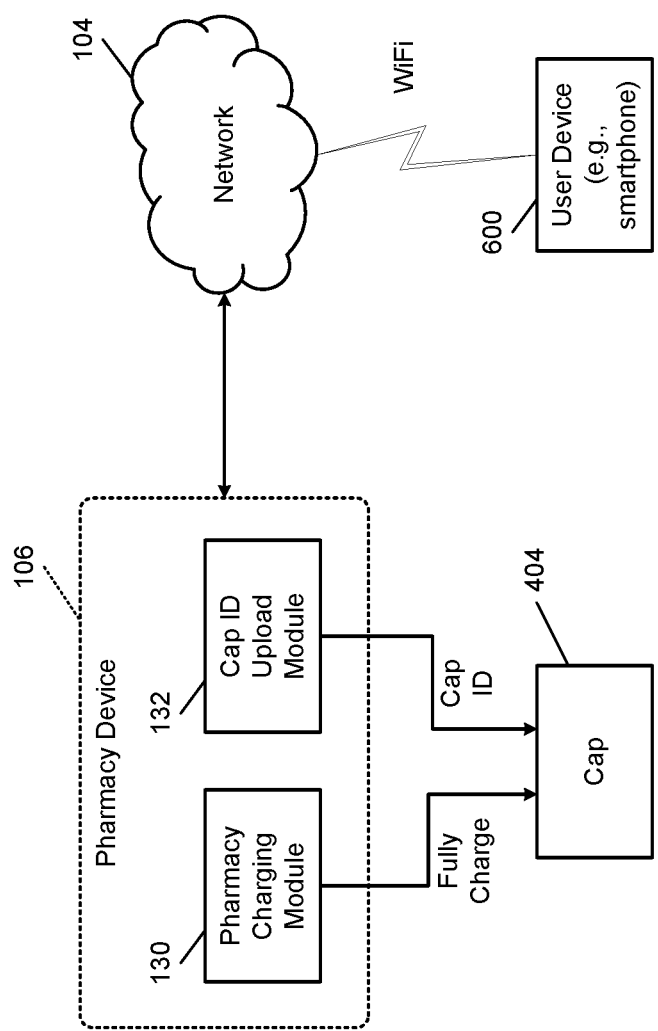
FIG. 6A is a functional block diagram of an example implementation of a cap charging system located at a pharmacy.

FIG. 6A is a functional block diagram of an example implementation of a cap charging system located at a pharmacy. The pharmacy charging module 132 of the pharmacy device 106 charges the battery of the cap 404 to a predetermined charge level. As indicated in FIG. 6A, the pharmacy charging module 130 fully charges the cap 404 if not already charged. The cap ID upload module 132 uploads a cap ID to the cap 404. In this way, the cap ID can be retrieved from the cap 404 to identify the cap 404. A user device 600—for example, a smartphone—communicates with the pharmacy device 106 via the network 104 using a WiFi connection. The user device 600 can be a mobile computing device, such as a phone, tablet, or another mobile computing device with a rechargeable battery capable of connecting to WiFi.

FIG. 6B is a functional block diagram of an example implementation of a wireless cap charging system located at a user's residence. A charging device 604 wirelessly charges the battery of the cap 404. In other implementations, the cap 404 is charged using a wired connection, such as via metal contacts. The charging device 604 may be portable and may be located at the user's residence. The cap 404 communicates with the user device 600 via a wireless connection, such as Bluetooth.

Figure 6C:
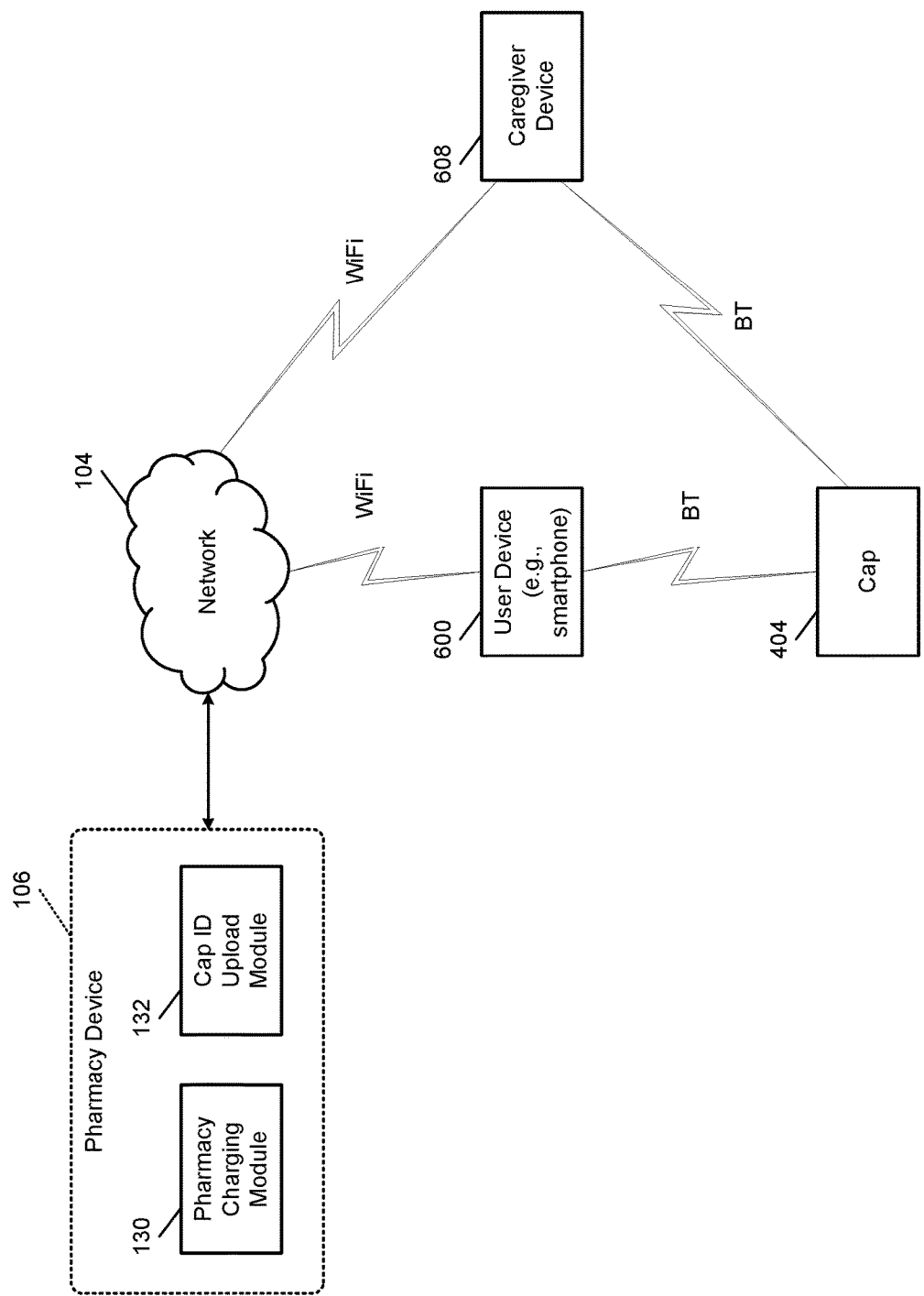
FIG. 6C is a functional block diagram of an example implementation of a delegation system at a user's residence.

FIG. 6C is a functional block diagram of an example implementation of a delegation system at a user's residence. In various implementations, a caregiver device 608 connects to the cap 404 after the user device 600 has delegated permission to the caregiver device 608. That is, after delegation, the caregiver device 608 directly communicates with the cap 404. The caregiver device 608 also communicates with the pharmacy device 106 via the network 104 using a WiFi connection. In various implementations, the caregiver device 608 is a mobile computing device, such as a phone, tablet, or another mobile computing device with a rechargeable battery capable of connecting to WiFi.

Figure 7A:
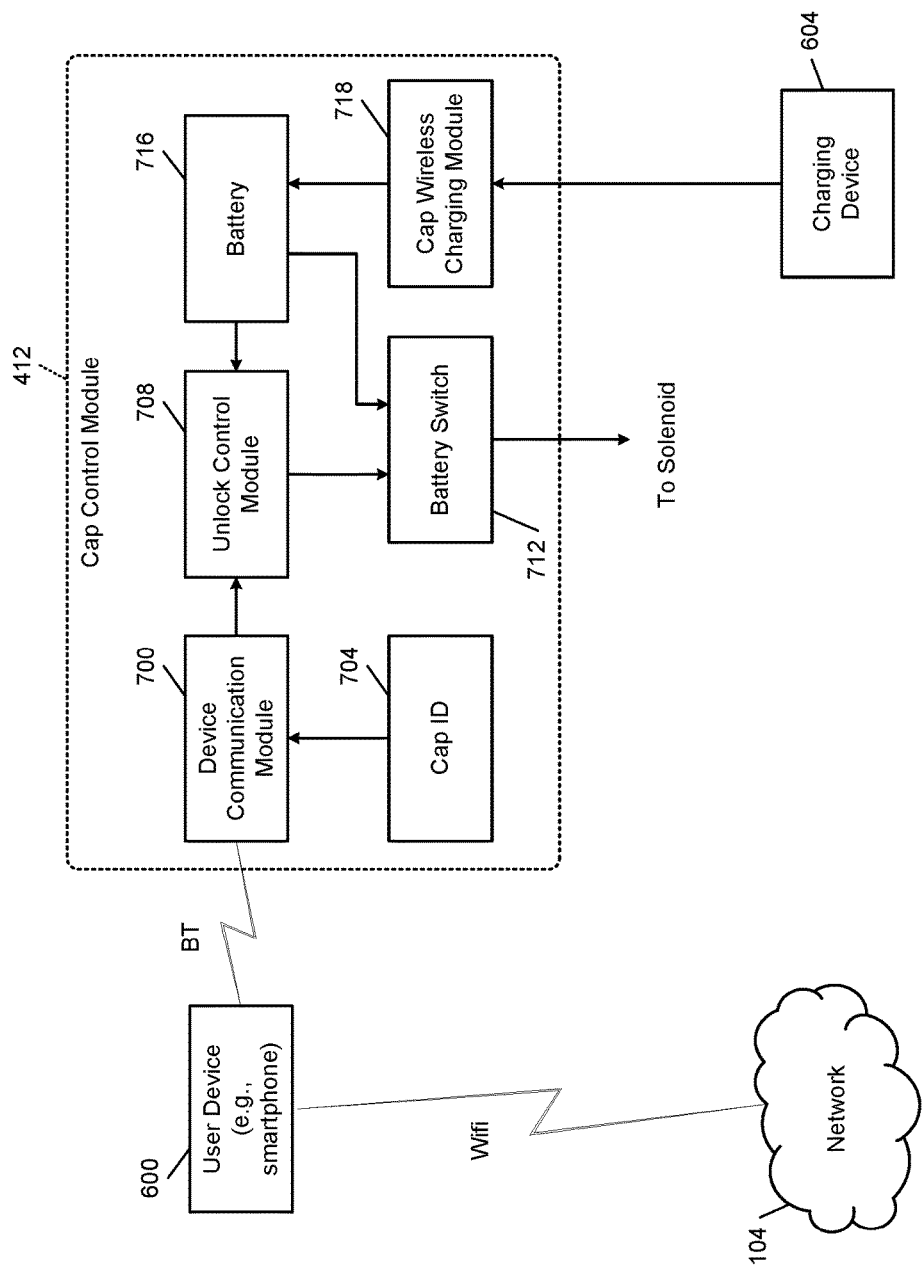
FIG. 7A is a functional block diagram of an example implementation of a cap control module of a locking cap.

FIG. 7A is a functional block diagram of an example implementation of the cap control module 412 of the cap. The cap control module 412 communicates with the user device 600 via a device communication module 700 using a Bluetooth connection. The device communication module 700 receives a cap ID 704 that indicates which cap is communicating with the user device 600. As mentioned previously, the cap ID 704 is uploaded to the cap at the pharmacy via the cap ID upload module.

An unlock control module 708 actuates a battery switch 712 based on control signals from the user device 600. The battery switch 712 connects a battery 716 to the solenoid, such as shown in FIGS. 4-5B. The battery 716 supplies current to the solenoid when the battery switch 712 is closed, unlocking the cap of the prescription container. The wireless charging device 604 charges the battery 716 via a cap wireless charging module 718. In various implementations, the wireless charging device 604 is a standalone device.

The user device 600 is operated by a user. The user device 600 can download and operate a prescription application. The user can select an option of the prescription application to unlock prescription containers prescribed to the user. Upon user input indicating a desire to open the prescription container, the user device 600 transmits an open prescription control signal, such as via a Bluetooth connection, to the cap control module 412 to permit access to the corresponding prescription container. The unlock control module 708 receives the open prescription control signal, such as via the device communication module 700, and actuates the battery switch 712. Once the prescription container is unlocked, the cap can be removed and the prescription administered.

Figure 7B:
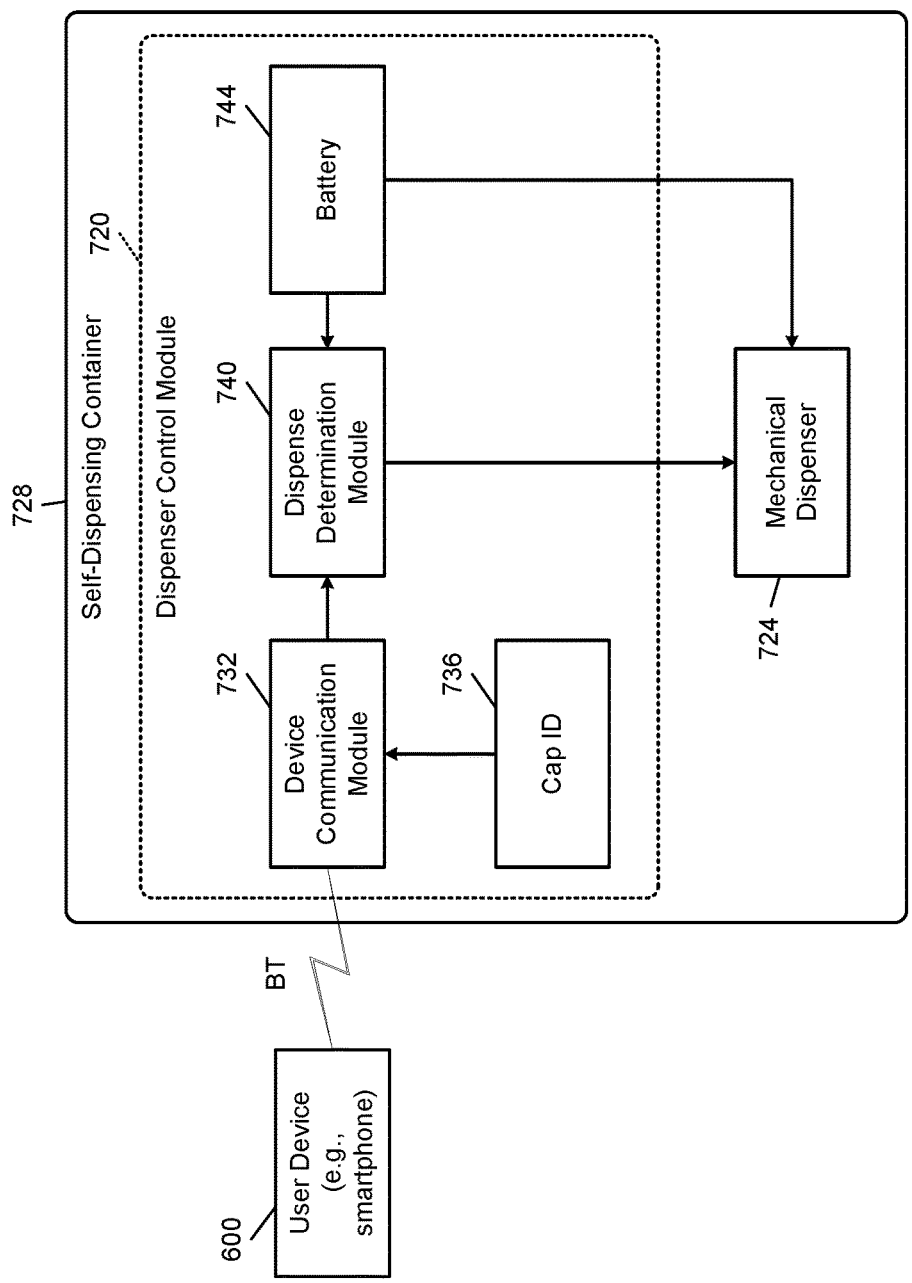
FIG. 7B is a functional block diagram of an example implementation of a dispenser control module of a mechanical dispenser.

FIG. 7B is a functional block diagram of an example implementation of a dispenser control module 720 of a mechanical dispenser 724. The dispenser control module 720 includes a self-dispensing container 728. The dispenser control module 720 determines an amount of a prescription drug to dispense: for example, a number of pills to dispense. The dispenser control module 720 includes a device communication module 732 to communicate with the user device 600. A cap ID 736 identifies the prescription drug in the self-dispensing container 728. Similar to the cap ID of FIG. 7A, the cap ID 736 is uploaded to the self-dispensing container 728 at the pharmacy. The device communication module 732 receives the cap ID 736 to identify the self-dispensing container 728 that is communicating with the user device 600.

A dispense determination module 740 transmits a dispense control signal to the mechanical dispenser 724 based on the dispense control signal received from the user device 600. The user can send the dispense control signal from the user device 600 when the user wants to access the prescription drug. The user device 600 communicates the dispense control signal to the dispense determination module 740 via the device communication module 732 using the Bluetooth connection.

In various implementations, the dispense determination module 740 may receive the dispense control signal and automatically transmit the dispense control signal to the mechanical dispenser 724 to dispense the appropriate amount of prescription. In various implementations, the dispenser control module 720 may include a set of dispensing parameters, such as a time or times the prescription may be dispensed based on regimen instructions of the corresponding prescription drug. The dispensing parameters must be satisfied prior to sending the dispense control signal. Once the dispense control signal is sent, the mechanical dispenser 724 dispenses the prescription drugs. A battery 744 supplies power to the dispense determination module 740 and the mechanical dispenser 724.

Figure 8:
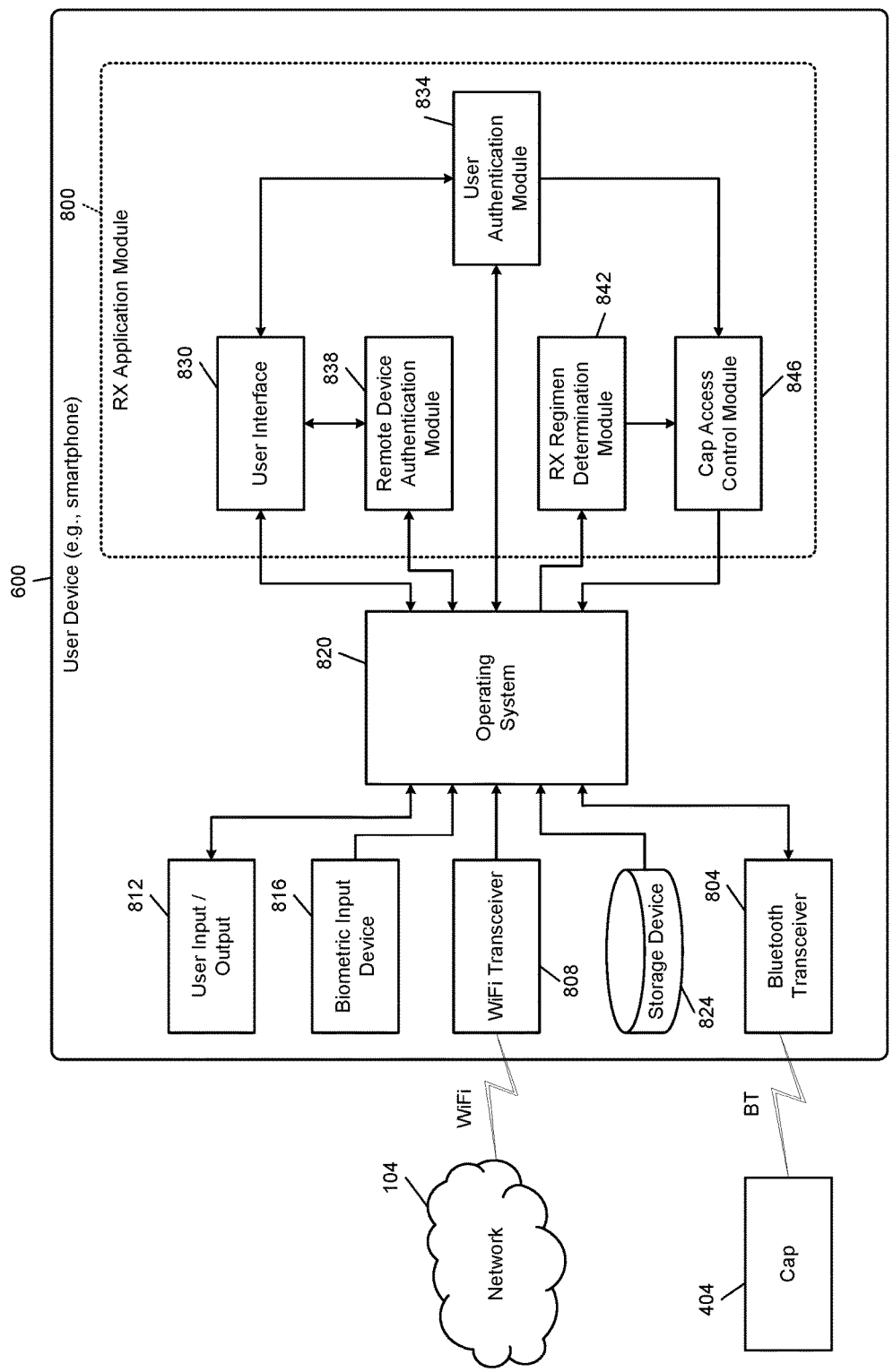
FIG. 8 is a functional block diagram of an example implementation of a prescription application module operating on a user device.

FIG. 8 is a functional block diagram of an example implementation of a prescription application module 800 operating on the user device 600. The user device 600 includes a Bluetooth transceiver 804 that communicates with the cap 404. The user device 600 also includes a WiFi transceiver 808 to communicate with the pharmacy device via the network 104. In this way, the WiFi transceiver 808 can obtain updated regimen instructions for the user's prescriptions.

The user device 600 receives user input from user input/output 812 and generates visual, audio, and/or tactical output via the user input/output 812. A biometric input device 816 receives biometric input from the user. For example, the biometric input could be a finger, a face, an iris, etc. The biometric input device 816 may be a fingerprint scanner or a front-facing camera to receive the corresponding biometric input.

The prescription application module 800 receives biometric-based authentication signals from the biometric input device 816 via the operating system 820. The prescription application module 800 receives regimen instructions for the user's prescriptions via the operating system 820 and the WiFi transceiver 808. The prescription application module 800 transmits open prescription control signals to the cap 404 via the Bluetooth transceiver 804 and the operating system 820. A storage device 824 stores biometric data of the user in a cryptographically-protected manner.

A user interface 830 displays different states of the prescription application through the operating system, which interacts with the user via the user input/output 812. The user interface 830 also receives user selections via the user input/output 812. A user authentication module 834 determines if a current biometric input from the biometric input device 816 matches the user's biometric input stored in the storage device 824. In other implementations, the operating system 820 may simply inform the user authentication module 834 whether the current biometric input matches the user's biometric input stored in the storage device 824, without revealing biometric data to the user authentication module 834 determines that the user has be validated.

A remote device authentication module 838 determines the validity of a remote device, such as the caregiver device 608 of FIG. 6C. When the user selects the prescription application option to delegate prescription opening authority to another device (such as, the caregiver device 608), the remote device authentication module 838 determines if the delegation to the caregiver device 608 is valid. In various implementations, the remote device authentication module 828 displays a code, for example, a QR code, using the user input/output 812. The caregiver device 608 then captures the code using a camera under the central copy of the prescription application downloaded on the remote device. The remote device authentication module 828 compares the code captured by the caregiver device 608 to the displayed code. If the codes match, the remote device is authenticated until the user revokes this delegation.

A prescription regimen determination module 842 receives regimen instructions of the user's prescriptions via the network 104. The cap access control module 846 can determine from the prescription regimen determination module 842 whether a prescription is currently active. If the prescription is currently active, the prescription application may display an open prescription option on the user interface 830. Then, in response to a user selection of the open prescription option, the cap access control module 846 will transmit the open prescription signal to the corresponding cap (for example, the cap 404) via the Bluetooth transceiver 804.

Application User Interface

Figure 9B:
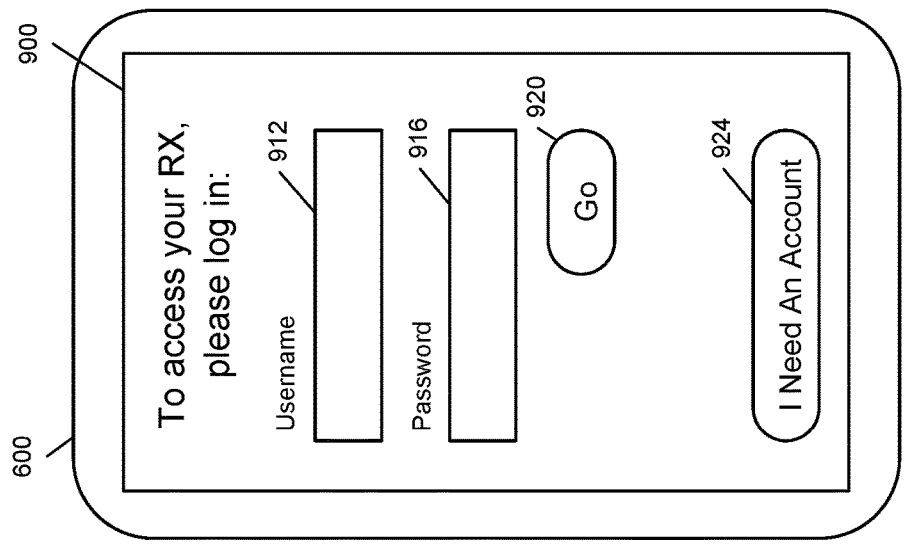
FIG. 9B is an example prescription application login screen of the prescription application.
Figure 9A:
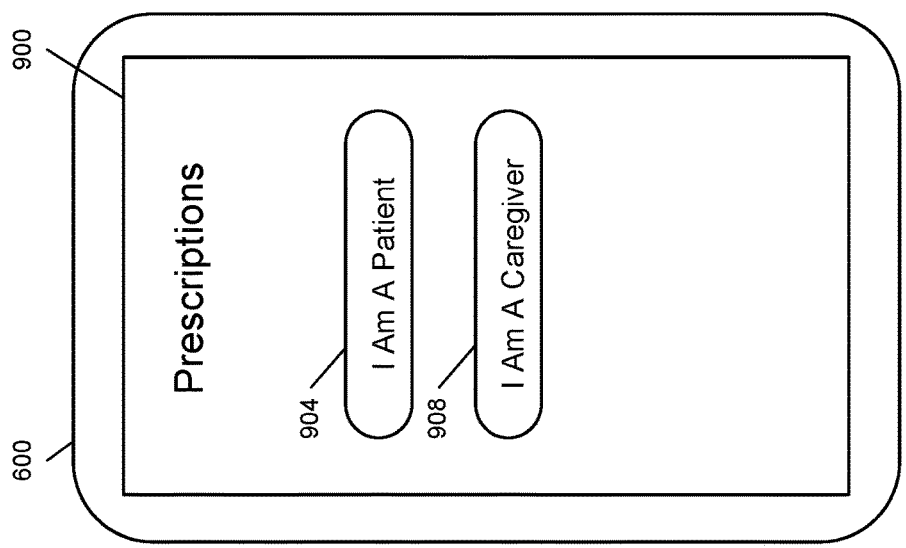
FIG. 9A is an example prescription application home screen of a prescription application.

FIG. 9A is an example prescription application home screen of the prescription application. Once the user has downloaded the prescription application on the user device 600 (or any other device that the user will use to open their prescriptions), the user selects the prescription application to launch the prescription application on a display screen 900 of the user device 600. A home screen is displayed on the display screen 900 and offers two selection options. The first option is to select a user button 904 displaying the phrase "I Am A Patient." The second option is to select a caregiver button 908 displaying the phrase "I Am A Caregiver." Selecting either the user button 904 or the caregiver button 908 directs the prescription application to a corresponding login screen, shown in FIG. 9B.

FIG. 9B is an example prescription application login screen of the prescription application. After the user has selected the user button 904 or the caregiver button 908, the prescription application is directed to the login screen of FIG. 9B. The screen 900 displays a username field 912 and a password field 916 where the user can enter their username and password and select a "Go" button 920. Alternatively, if the user has not created an account, the user can select a create account button 924 that displays the phrase "I Need An Account." After selecting the create account button 924, the user can enter their details to verify their identity and set up an account. The prescription application can retrieve prescription information for the user based on user details entered to create the account. Once the user has logged in, the user is directed to a user screen (shown in FIG. 9C) or a caregiver screen (shown in FIG. 9D).

Figure 9D:
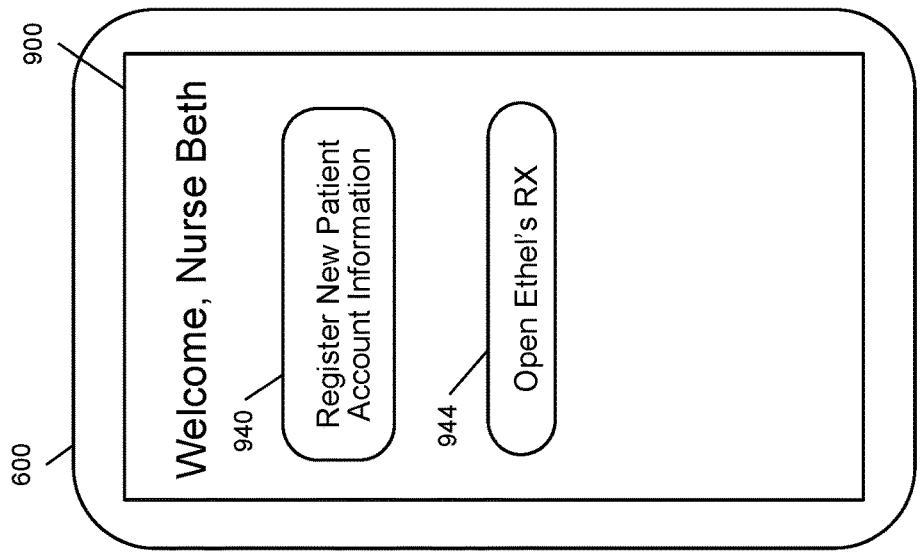
FIG. 9D is an example prescription application caregiver screen of the prescription application.
Figure 9C:
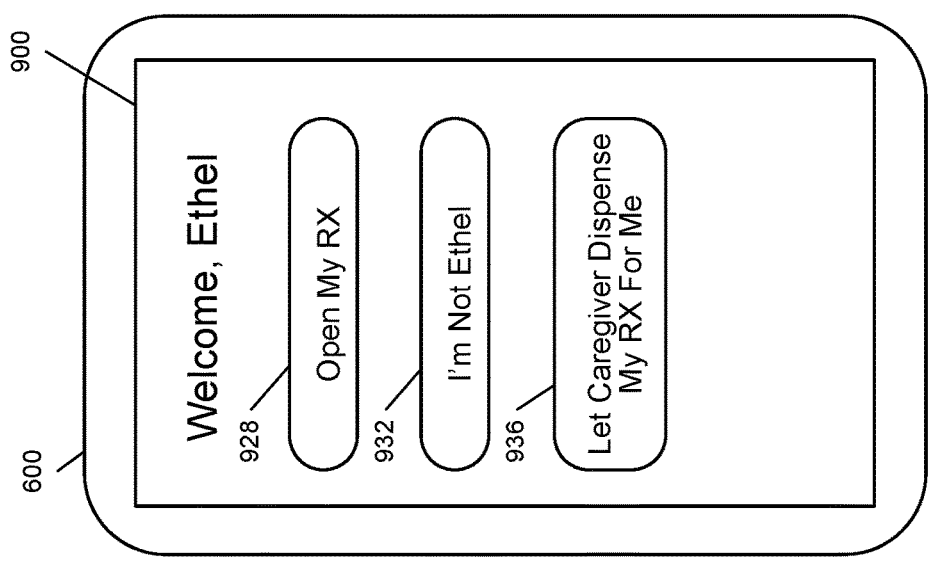
FIG. 9C is an example prescription application user screen of the prescription application.

FIG. 9C is an example prescription application user screen of the prescription application. Once the user (in this example, Ethel) is logged in, the user is presented with a list of the following options: an open my prescription button 928, a different user button 932, and a delegation button 936. The open my prescription button 928 displays the phrase "Open My RX" and, upon selection, directs the user to a list of prescriptions as depicted in FIG. 9E. The different user button 932 displays the phrase "I'm Not Ethel" and, upon selection, logs out of the current account and directs the prescription application to the log on screen of FIG. 9B. The delegation button 936 displays the phrase "Let Caregiver Dispense My RX For Me" and, upon selection, initiates the process of authorizing a caregiver device to dispense the user's prescriptions.

FIG. 9D is an example prescription application caregiver screen of the prescription application. Upon selection of the caregiver button 908 of FIG. 9A, the prescription application displays a welcome screen for the caregiver: for example, Nurse Beth. The caregiver can select a register new user button 940 or an open prescription button 944. The register new user button 940 displays the phrase "Register New Patient Account Information" and, upon selection, the caregiver is prompted to insert account information of the new user. If the caregiver is opening a prescription for an existing user, such as Ethel, the caregiver can select the open prescription button 944 displaying the phrase "Open Ethel's RX." Multiple open prescription buttons can be displayed on the screen 900 for different users.

FIG. 9E is an example prescription application prescription selection screen of the prescription application. Upon selection of the open my prescription button 928 of FIG. 9C or the open prescription button 944 of FIG. 9D, the prescription application displays a screen including a list of prescription drugs for the selected user. The list of drugs may include, for example, atorvastatin calcium 948-1, levothyroxine 948-2, lisinopril 948-3, omeprazole 948-4, and metformin 948-5 (collectively, active prescriptions 948). Upon selection of one of the active prescriptions 948, the prescription application will transmit an open prescription control signal to the corresponding cap to permit access the appropriate prescription. In various implementations, the prescription application will transmit a dispense signal to the corresponding self-dispensing container.

Figure 9F:
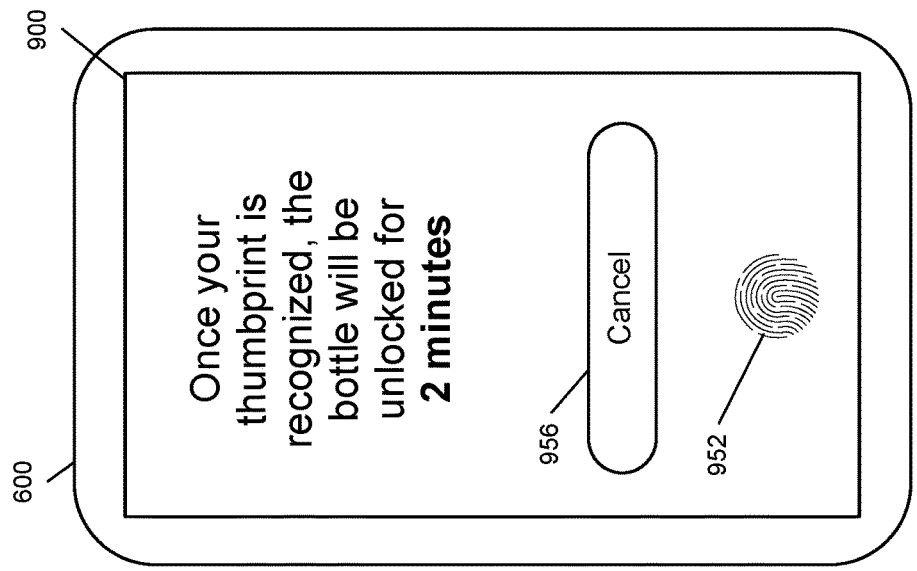
FIG. 9F is an example prescription application biometric request screen of the prescription application.
Figure 9E:
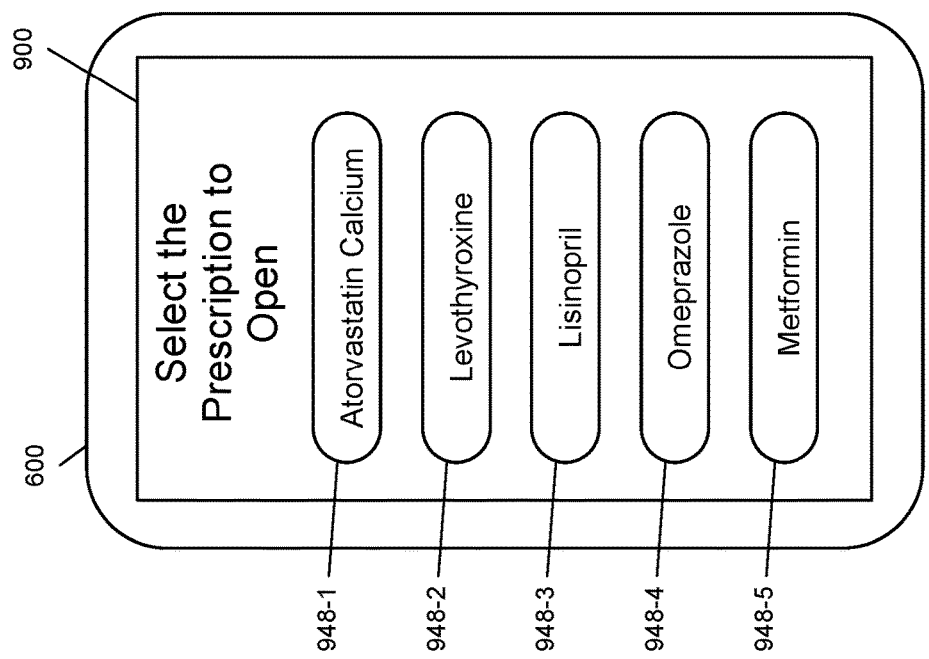
FIG. 9E is an example prescription application prescription selection screen of the prescription application.

FIG. 9F is an example prescription application biometric request screen of the prescription application. Upon selection of one of the active prescriptions 948 of FIG. 9E, the user or caregiver is prompted to provide biometric input to validate the user's authorization to unlock (or, in the case of mechanical dispenser, dispense) the selected prescription. In various implementations, the unlocking will last for a limited time, such as, two minutes. A cancel button 956 is also displayed to cancel the authentication request. Once the biometric input is verified, an open signal is transmitted to the corresponding cap.

FIG. 9G is an example prescription application user delegation screen of the prescription application. Upon selection of the register new user button 940 of FIG. 9D and verification of the user (for example, in a screenshot similar to FIG. 9F), the prescription application displays a QR code 960 to authorize the caregiver device 608. As previously discussed, when delegating to the caregiver, the user device 600 displays the QR code 960 and the caregiver device captures the QR code 960 to authenticate the caregiver device 608. In various implementations, the QR code 960 will be displayed for a predetermined timeout, such as 30 seconds. The user may select a cancel button 964 once the caregiver device has captured the QR code 960 or to hide the QR code 960 before the timeout expires.

Flowcharts

Figure 10A:
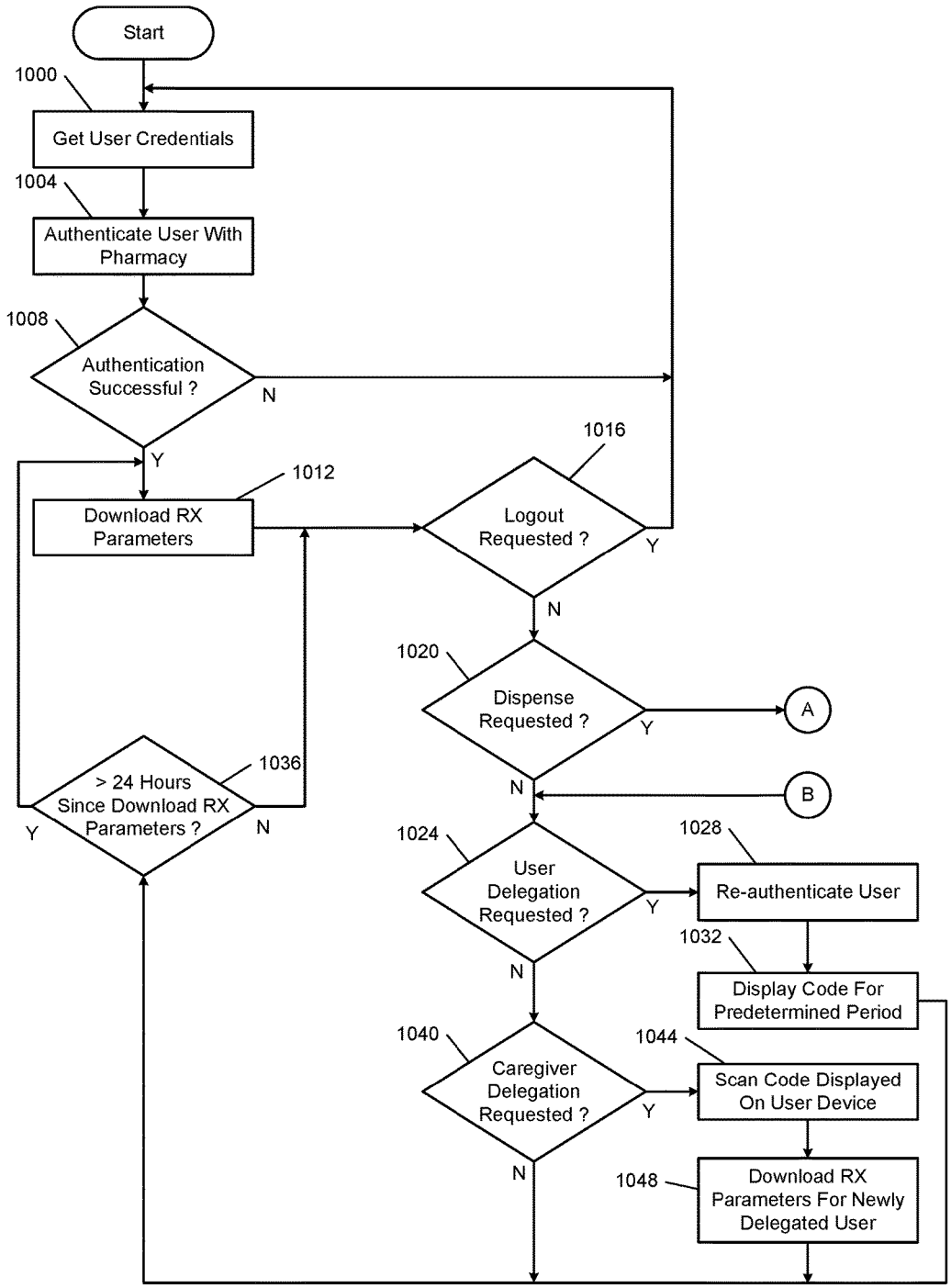
FIG. 10A is a flowchart of example prescription application login operation according to the prescription application.

FIG. 10A is a flowchart of example prescription application login operation. Control begins at 1000 where the user logs in to the prescription application by supplying user credentials. At 1004, control authenticates the user credentials with the pharmacy. At 1008, control determines if the authentication was successful. If so, control continues to 1012 to download prescription parameters; otherwise, control returns to 1000 to continue to wait for correct user credentials.

At 1012, control retrieves prescription parameters of the prescriptions of the user includes regimen instructions corresponding to each active prescription. The prescription application can store the prescription parameters for each prescription. After downloading the prescription parameters at 1012, control continues to 1016 to determine if a logout has been requested. If yes, control returns to 1000 to wait for the user to log in; otherwise, control continues to 1020 to determine if a drug dispense has been requested. The drug dispense may be in the form of unlocking the cap, as depicted in FIGS. 4-5B.

Figure 10B:
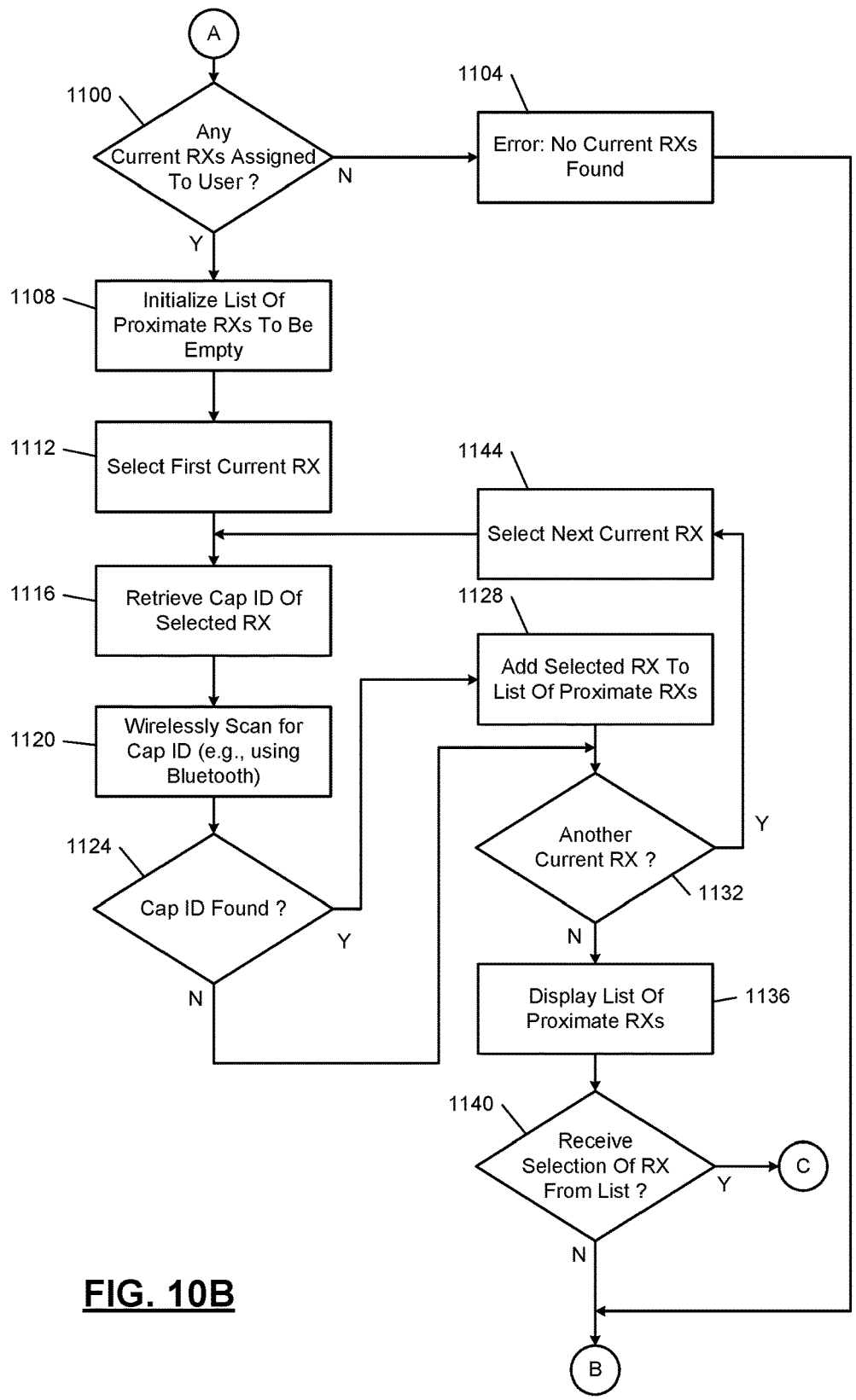
FIG. 10B is a flowchart of example proximate prescription identification according to the prescription application.

If the drug dispense is requested at 1020, control continues to FIG. 10B. Alternatively, if the drug dispense was not requested, control continues to 1024, where control determines if a user delegation request is selected. If the user delegation request has been received, control continues to 1028 to re-authenticate the user. For example, to re-authenticate, the user is requested to submit biometric input to verify the user's identity, similar to what is shown in FIG. 9F. Once re-authenticated, control continues to 1032 to display a code for a predetermined period, as shown in FIG. 9G. After the code is displayed for the predetermined period at 1032, control proceeds to 1036.

At 1036, control determines if 24 hours have passed since last downloading the prescription parameters. If yes, control returns to 1012 to download (or check for updates of) the prescription parameters to ensure the most up-to-date prescription parameters are downloaded to the prescription application. Otherwise, control returns to 1016 to determine if a logout has been requested.

Returning to 1024, control determines if there has been a user delegation request. If no delegation request was received, control continues to 1040 to determine if the caregiver has requested delegation. That is, control determines if the caregiver has selected to register a new user and receive delegation permissions from that user. If at 1040 a caregiver delegation request is received, control continues to 1044 where the code displayed on the user device is captured by the caregiver device. Then control proceeds to 1048 to download the prescription parameters for the newly delegated user. If at 1040 the caregiver delegation was not requested, control continues to 1036 to determine if control should update the prescription parameters.

FIG. 10B is a flowchart of example proximate prescription identification. In FIG. 10A at 1020, control determines if a dispense request is received, and, if so, continues to FIG. 10B at 1100 where control determines if any current prescriptions are assigned to the user. If no, control proceeds to 1104 and displays an error indicating that no current prescriptions were found. If no current prescriptions were found, control then returns to 1024 of FIG. 10A, as if no dispense was requested.

If control determines at 1100 that current prescriptions are assigned to the user, control proceeds to 1108 to initialize a list of proximate prescriptions to be empty. That is, the list of proximate prescriptions is initialized and empty. Control proceeds to 1112 to select a first current prescription from the current prescriptions assigned to the user. Control continues to 1116 to retrieve a cap ID of the selected prescription. As shown in FIGS. 7A-7B, each cap includes a cap ID identifying the cap, user, and prescription information. After retrieving the cap ID, control wirelessly scans for the cap ID at 1120. For example, control can wirelessly scan using Bluetooth.

If the cap ID is found at 1124 control adds the selected prescription to the list of proximate prescriptions, indicating the cap ID is close enough to the user device to wirelessly connect using a near field communications protocol, such as Bluetooth. Once the selected prescription is added to the list of proximate prescriptions at 1128 or if the cap ID is not found, control continues to 1132 to determine if another current prescription is assigned to the user. If no further prescriptions are active, control continues to 1132 to display the list of proximate prescriptions (as demonstrated in FIG. 9E) and waits to receive a selection of one of the prescriptions displayed on the list of proximate prescriptions at 1140. Once a selection is received, control continues to FIG. 10C to dispense the selected drug. If no selection in received, control returns to 1024 of FIG. 10A. However, if there is another current prescription at 1132, control continues to 1144 to select the next current prescription assigned to the user. Then control returns to 1116.

Figure 10C:
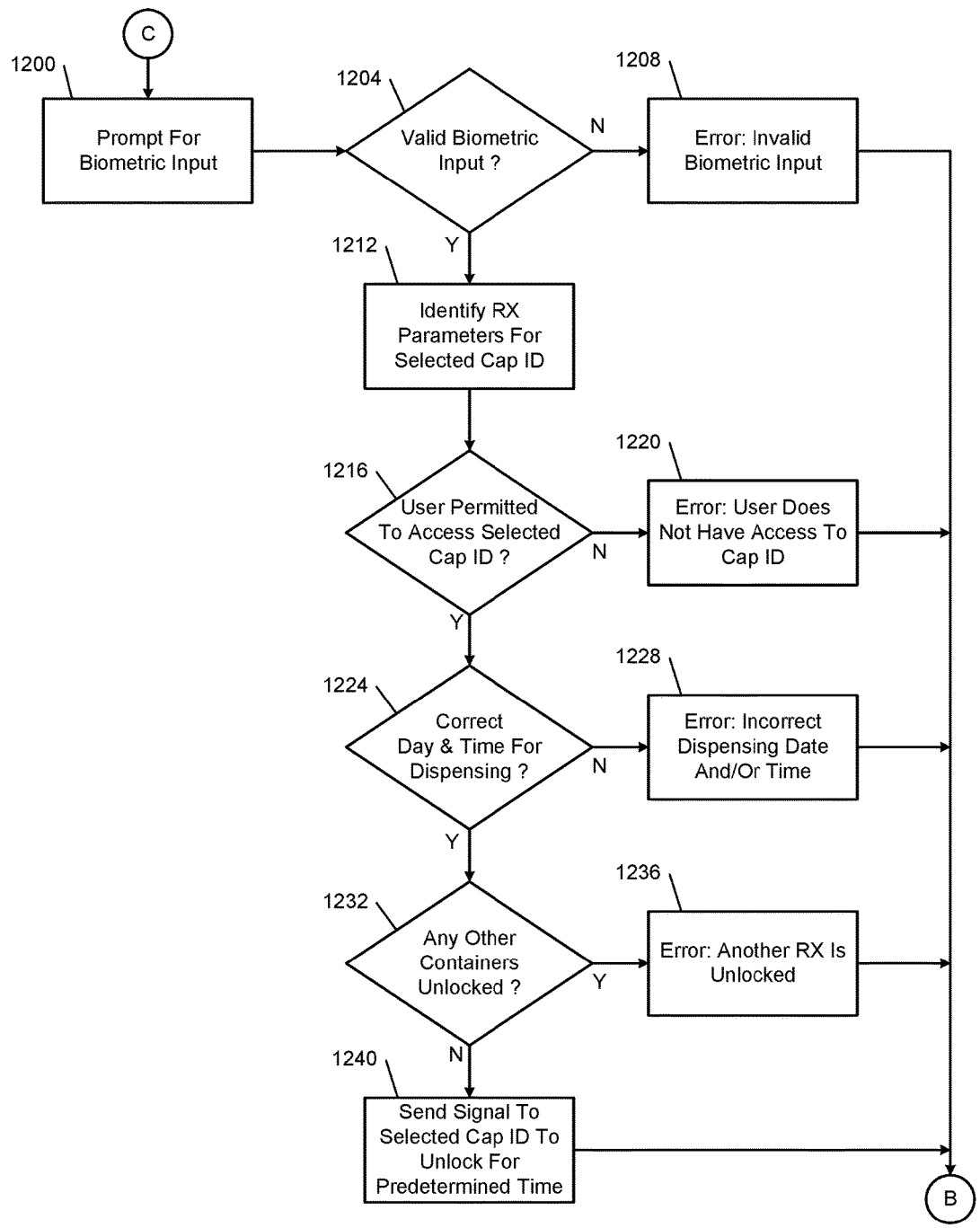
FIG. 10C is a flowchart of example prescription container opening according to the prescription application.

FIG. 10C depicts example prescription container opening operation. Control begins at 1200 after the user has made a selection of a prescription from the list of proximate prescriptions at 1140 in FIG. 10B. At 1200, the user is prompted for biometric input, for example, the screen displayed in FIG. 9F. At 1204, control determines if the biometric input is valid. If no, control proceeds to 1208 to issue an error indicating invalid biometric input. Control continues to 1024 of FIG. 10A to determine if a user delegation was requested. However, if the biometric input at 1204 is valid, control continues to 1212 to identify prescription parameters for the selected cap ID. As previously discussed, the prescription parameters are determined from the regimen instructions retrieved from the pharmacy.

Control continues to 1216 to determine if the user is permitted to access the selected cap ID. That is, control determines if the cap ID is a current prescription of the user based on information retrieved from the pharmacy. If no, control proceeds to 1220 to issue an error indicating that the user does not have access to the selected cap ID and then proceeds to 1024 of FIG. 10A. For example, the user could be a caregiver who does not have the required authorization to unlock or dispense from a particular prescription container. Otherwise, if the user is permitted to access the selected cap ID, control continues to 1224 to determine if the current day and time is a correct day and time for dispensing the prescription of the selected cap ID based on the prescription parameters. For example, if the selected cap ID is associated with prescription parameters that instruct the prescription is to be taken Monday, Wednesday, and Friday, control determines if the current day matches one of the days to administer the prescription drugs. If access is not currently permitted, control issues an error indicating an incorrect dispensing date and/or time at 1228 and returns to 1024 of FIG. 10A.

Otherwise, if the day and time satify the prescription parameters, control continues to 1232 to determine if any other containers issued to the user are unlocked. In this way, control prevents multiple caps from being removed at the same time to avoid a cap from being attached to the wrong bottle. If other containers are unlocked at 1232, control continues to 1236 to issue an error indicating that another prescription is unlocked. Otherwise, at 1240, control sends the open signal to the selected cap ID to unlock the cap for a predetermined time. Then, control returns to 1024 of FIG. 10A.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules, circuit elements, semiconductor layers, etc.) are described using various terms, including "connected," "engaged," "coupled," "adjacent," "next to," "on top of," "above," "below," and "disposed." Unless explicitly described as being "direct," when a relationship between first and second elements is described in the above disclosure, that relationship can be a direct relationship where no other intervening elements are present between the first and second elements, but can also be an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A.

In this application, including the definitions below, the term "module" or the term "controller" may be replaced with the term "circuit." The term "module" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Some or all hardware features of a module may be defined using a language for hardware description, such as IEEE Standard 1364-2005 (commonly called "Verilog") and IEEE Standard 1076-2008 (commonly called "VHDL"). The hardware description language may be used to manufacture and/or program a hardware circuit. In some implementations, some or all features of a module may be defined by a language, such as IEEE 1666-2005 (commonly called "SystemC"), that encompasses both code, as described below, and hardware description.

The term code, as used above, may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

What is claimed is:

1. A locking container access system comprising:
at least one processor; and
a memory storing instructions for execution on the at least one processor, wherein the instructions include:
establishing a connection to a locking container and obtaining an identifier from the locking container, wherein the locking container includes a bottle and a cap that attaches to the bottle, and wherein the connection is established with the cap; and
in response to a user authenticating to the locking container access system:
establishing a remote networking connection to an access control system;
obtaining access parameters for the user from the access control system; and
in response to receiving an open instruction from the user for the locking container, (i) requesting verification of the user based on biometric information of the user, (ii) determining whether the identifier is included in the access parameters, and (iii) in response to determining that the identifier is included in the access parameters and successful verification of the user based on the biometric information, transmitting an open command to the locking container.

2. The locking container access system of claim 1 wherein:
the access parameters include an expiration date; and
the instructions include preventing transmission of the open command subsequent to the expiration date.

3. The locking container access system of claim 1 wherein:
the access parameters include one or more times of day; and
the instructions include preventing transmission of the open command at a time not within the one or more times of day.

4. The locking container access system of claim 1 wherein the user authenticates to the locking container access system by supplying a username and password.

5. The locking container access system of claim 1 wherein:
the instructions include, in response to a delegation instruction from the user, displaying a unique code for capture by a second device; and
the unique code enables access to the locking container by the second device.

6. The locking container access system of claim 1 wherein the instructions include:
establishing connections with a plurality of locking containers including the locking container;
based on the access parameters, determining a set of containers associated with the user from among the plurality of locking containers; and
displaying a list of the set of containers to the user for potential unlocking.

7. The locking container access system of claim 1 wherein the open command instructs the cap to disengage from the bottle so that the cap can rotate with respect to the bottle.

8. The locking container access system of claim 1 wherein:
the bottle includes prescribed items; and
the access control system is maintained by a pharmacy that fulfilled a prescription for the prescribed items.

9. The locking container access system of claim 1 wherein:
the connection to the locking container is established according to a BLUETOOTH wireless networking standard; and
the remote networking connection is established over the internet.

10. The locking container access system of claim 1 wherein:
the open command instructs the locking container to remain unlocked for a predetermined period of time; and
transmission of the open command prevents future transmission of open commands for the predetermined period of time.

11. A method of accessing a locking container, the method comprising:
establishing a connection to the locking container;
obtaining an identifier from the locking container; and
in response to receiving an indication that a user has authenticated to a locking container access system:
establishing a remote networking connection to an access control system;
obtaining access parameters for the user from the access control system, wherein the access parameters include an expiration date; and
in response to receiving an open instruction from the user for the locking container, (i) requesting verification of the user based on biometric information of the user, (ii) determining whether the identifier is included in the access parameters, and (iii) in response to determining that the identifier is included in the access parameters and successful verification of the user based on the biometric information, transmitting an open command to the locking container, wherein transmission of the open command is prevented subsequent to the expiration date.

12. The method of claim 11 wherein the access parameters include one or more times of day, and wherein transmission of the open command is prevented at a time not within the one or more times of day.

13. The method of claim 11 wherein the user authenticates to the locking container access system by supplying a username and password.

14. The method of claim 11 further comprising, in response to a delegation instruction from the user, displaying a unique code for capture by a second device, wherein the unique code enables access to the locking container by the second device.

15. The method of claim 11 wherein:
the establishing the connection includes establishing connections with a plurality of locking containers including the locking container;
the method further comprises, based on the access parameters, determining a set of containers associated with the user from among the plurality of locking containers; and
the method further comprises displaying a list of the set of containers to the user for potential unlocking.

16. The method of claim 11 wherein:
the locking container includes (i) a bottle containing prescribed items and (ii) a cap that attaches to the bottle;
the access control system is maintained by a pharmacy that prescribed the bottle;
the connection is established with the cap; and
the open command instructs the cap to disengage from the bottle so that the cap can rotate with respect to the bottle.

17. The method of claim 11 wherein:
the open command instructs the locking container to remain unlocked for a predetermined period of time; and
transmission of the open command prevents future transmission of open commands for the predetermined period of time.

18. A non-transitory computer-readable medium storing processor-executable instructions, the instructions comprising:
establishing a connection to a locking container;
obtaining an identifier from the locking container; and
in response to receiving an indication that a user has authenticated to a locking container access system:
establishing a remote networking connection to an access control system;
obtaining access parameters for the user from the access control system;
in response to receiving an open instruction from the user for the locking container, (i) requesting verification of the user based on biometric information of the user, (ii) determining whether the identifier is included in the access parameters, and (iii) in response to determining that the identifier is included in the access parameters and successful verification of the user based on the biometric information, transmitting an open command to the locking container; and in response to a delegation instruction from the user, displaying a unique code for capture by a second device, wherein the unique code enables access to the locking container by the second device.

19. The non-transitory computer-readable medium of claim 18 wherein:

the locking container includes a bottle and a cap that attaches to the bottle; and the connection is established with the cap.

20. The non-transitory computer-readable medium of claim 18 wherein:

the locking container is a bottle including prescribed items; and the access control system is maintained by a pharmacy that fulfilled a prescription for the prescribed items.

\* \* \* \* \*